(12) United States Patent
Furuishi et al.

(10) Patent No.: US 9,050,247 B2
(45) Date of Patent: Jun. 9, 2015

(54) PHARMACEUTICAL COMPOSITION FOR EXTERNAL USE

(75) Inventors: Takayuki Furuishi, Tokyo (JP); Kazuo Tomono, Tokyo (JP); Toyofumi Suzuki, Tokyo (JP); Toshiro Fukami, Tokyo (JP); Koji Kunimasu, Ono (JP)

(73) Assignees: NIHON UNIVERSITY, Tokyo (JP); NIPPON ZOKI PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 13/509,391

(22) PCT Filed: Nov. 11, 2010

(86) PCT No.: PCT/JP2010/070137
§ 371 (c)(1),
(2), (4) Date: Jun. 25, 2012

(87) PCT Pub. No.: WO2011/059037
PCT Pub. Date: May 19, 2011

(65) Prior Publication Data
US 2012/0264742 A1    Oct. 18, 2012

(30) Foreign Application Priority Data
Nov. 12, 2009  (JP) ................................. 2009-259073

(51) Int. Cl.
| | |
|---|---|
| A61K 47/14 | (2006.01) |
| A61K 31/135 | (2006.01) |
| A61P 25/04 | (2006.01) |
| A61K 9/00 | (2006.01) |
| A61K 31/439 | (2006.01) |
| A61K 31/485 | (2006.01) |
| A61K 31/55 | (2006.01) |
| A61K 9/06 | (2006.01) |
| A61K 9/70 | (2006.01) |

(52) U.S. Cl.
CPC ............. *A61K 9/0014* (2013.01); *A61K 31/135* (2013.01); *A61K 31/439* (2013.01); *A61K 31/485* (2013.01); *A61K 31/55* (2013.01); *A61K 47/14* (2013.01); *A61K 9/06* (2013.01); *A61K 9/7038* (2013.01); *A61K 9/7061* (2013.01); *A61K 9/7084* (2013.01)

(58) Field of Classification Search
None
See application file for complete search history.

(56) References Cited

U.S. PATENT DOCUMENTS

| | | | |
|---|---|---|---|
| 4,263,313 A | 4/1981 | Eckert et al. | |
| 4,749,574 A | 6/1988 | Ueda et al. | |
| 6,090,405 A | 7/2000 | Ninomiya et al. | |
| 2005/0191328 A1* | 9/2005 | Taniguchi | 424/401 |
| 2005/0191338 A1* | 9/2005 | Kang et al. | 424/449 |
| 2008/0076789 A1* | 3/2008 | Stinchcomb et al. | 514/282 |
| 2010/0003312 A1* | 1/2010 | Kanebako et al. | 424/447 |

FOREIGN PATENT DOCUMENTS

| | | | |
|---|---|---|---|
| CN | 101564383 | * | 10/2009 |
| CN | 101564383 A | | 10/2009 |
| JP | A-53-107409 | | 9/1978 |
| JP | A-60-075405 | | 4/1985 |
| JP | A-63-045219 | | 2/1988 |
| JP | A-01-301617 | | 12/1989 |
| JP | A-04-275215 | | 9/1992 |
| JP | A-10-036265 | | 2/1998 |
| JP | A-11-189545 | | 7/1999 |
| JP | A-2000-103722 | | 4/2000 |
| JP | A-2002-020315 | | 1/2002 |
| JP | A-2003-128510 | | 5/2003 |
| JP | A-2006-248996 | | 9/2006 |
| WO | WO 97/14411 A1 | | 4/1997 |
| WO | WO 03/094917 A1 | | 11/2003 |
| WO | WO 2006/085521 A1 | | 8/2006 |
| WO | 2008/105445 A1 | | 9/2008 |

OTHER PUBLICATIONS

Furuishi (Effects of caprylic acid monoglyceride on transdermal absorption of eptazocine, 126 Abstracts Ann. Meet. Pharm. Soc. Japan 133 (2006)).*
Mar. 8, 2011 International Search Report issued in Application No. PCT/JP2010/070137.
Furuishi, et al., "Effects of Caprylic Acid Monoglyceride on Transdermal Absorption of Eptazocine," *Abstracts of Annual Meeting of Pharmaceutical Society of Japan*, 2006, pp. 133, vol. 126, No. 2 (with translation).
Fukushima, et al., "Effects of Combination Use of Isopropyl Myristate/Caprylic Acid Monoglyceride on Skin Permeability of Eptazocine," *Abstracts of Annual Meeting of Pharmaceutical Society of Japan*, Mar. 5, 2009, pp. 286, vol. 129, No. 4 (with translation).
Furuishi, et al., "Effects of Enhancers on Transdermal Absorption of Eptazocine Hydrobromide," *Abstracts of Annual Meeting of Pharmaceutical Society of Japan*, 2007, pp. 111, vol. 127, No. 3 (with translation).

(Continued)

*Primary Examiner* — H. Sarah Park
(74) *Attorney, Agent, or Firm* — Oliff PLC

(57) ABSTRACT

A pharmaceutical composition for external use which is an organogel containing a fatty acid ester and a glycerolglycerin fatty acid ester, in particular, a novel transdermally absorbabedle pharmaceutical composition for external use which has a drug such as non-narcotic analgesics as an active ingredient made in organogel form containing a drug such as non-narcotic analgesics as an active ingredient, a fatty acid ester and a glycerolglycerin fatty acid ester, and a method for producing the composition. The pharmaceutical composition significantly improves skin permeability of drugs such as non-narcotic analgesics and allows a sufficient amount of drug to permeate the skin sustainably. Moreover, since the pharmaceutical composition is in organogel form, it can be easily applied to a preparation in practice. In addition, the pharmaceutical composition can provide efficient use and the like of drugs due to a high drug release rate and therefore is highly useful.

16 Claims, 8 Drawing Sheets

(56) References Cited

OTHER PUBLICATIONS

Furuishi et al., "Effect of Permeation Enhancers on the in Vitro Percutaneous Absorption of Pentazocine," Biol. Pharm. Bull., vol. 30, No. 7, pp. 1350-1353, 2007.

Feb. 11, 2015 Supplementary European Search Report issued in European Application No. 10829996.7.

Vintiloiu et al., "Organogels and Their Use in Drug Delivery—A Review," Journal of Controlled Release, vol. 125, pp. 179-192, 2008.

* cited by examiner

PHARMACEUTICAL COMPOSITION FOR EXTERNAL USE

TECHNICAL FIELD

The present invention relates to a pharmaceutical composition for external use having excellent skin permeability of drugs and a method for producing the composition.

BACKGROUND ART

Conventionally, non-narcotic analgesics have been administered to patients in dosage forms such as oral, injectable and suppository preparations. However, oral preparations may have the problem of poor absorption, low bioavailability or the like, whereas injectable preparations have the disadvantage of requiring frequent administration and therefore causing pain and inconvenience to patients. On the other hand, although suppository preparations improve the above disadvantages of oral and injectable preparations in some ways, they have the disadvantage of great inconvenience and discomfort of patients due to the administration route.

In recent years, a wide variety of studies on transdermal absorption of drugs have been carried out in order to solve the disadvantages of various dosage forms as described above and moreover to use the characteristics of transdermal administration preparations that can deliver drugs at a controlled rate for a long term compared with injectable preparations and oral administration preparations. However, when drugs are administered transdermally, there is the fundamental problem that it is difficult to improve skin permeability of drugs since the stratum corneum on the skin surface has a barrier function against drug permeation. Therefore, it is essential to enhance the transdermal absorbability of drugs in some way so as to allow drugs to be absorbed transdermally in an effective manner. In order to solve this problem, there have been studied and developed absorption enhancers and transdermal absorption devices.

For example, eptazocine, which is one of non-narcotic analgesics, is used for various types of cancer pain, postoperative pain and the like, and has excellent characteristics of fewer side effects such as physical dependence and respiratory depression compared with other non-narcotic analgesics. Currently, only injectable preparations of eptazocine hydrobromide are commercially available as eptazocine preparations. However, injectable preparations require frequent administration due to its short half-life in blood and therefore cause pain to patients upon administration, and also require patients to go to hospital regularly, resulting in inconvenience. For these reasons, there is a demand for the development of preparations for external use which allow a therapeutically sufficient amount of drugs to be absorbed transdermally in a sustained manner; however, hitherto there has been no technique to increase the transdermal absorbability in a sustained manner to a practical level, so that such preparations for external use have not been put into practical use.

As for transdermally absorbed preparations of non-narcotic analgesics, Patent Document 1 discloses that the combined use of pentazocine with isopropyl myristate and caprylic acid monoglyceride (glyceryl monocaprylate) which are transdermal absorption enhancers improves the skin permeability. In a scientific meeting, there has been reported a composition containing isopropyl myristate and a glycerin fatty acid ester which are the same as the transdermal absorption enhancers used in Patent Document 1 in addition to eptazocine (See Non-Patent Document 1). However, as described in both documents, pharmaceutical compositions containing pentazocine or eptazocine and, as absorption enhancers, a fatty acid ester such as isopropyl myristate and a glycerin fatty acid ester such as caprylic acid monoglyceride are all in the form (dosage form) of a liquid (solution or suspension). Drugs in liquid dosage form may be excellent in skin permeability in some cases; however, such drugs themselves are difficult to be applied as a preparation for external use which exerts drug efficacy sustainably for a long term.

Accordingly, the present inventors have tried to formulate the eptazocine-containing pharmaceutical composition in suspension form described in Non-Patent Document 1 into a patch preparation. In the case of suspensions, there is the problem that suspensions should be made into patch preparations by maintaining their uniformly dispersed state. Therefore, the present inventors have produced a matrix-type patch preparation which is a transdermal administration preparation that can uniformly disperse and hold drugs. As for acrylic adhesives which are most commonly used as a matrix, the present inventors have produced matrix-type patch preparations with various acrylic adhesives and tested their transdermal absorbability; however, good results have not been obtained. That is, even with eptazocine-containing matrices, each having a high concentration of 10% or 20% by weight, the skin permeation rate of eptazocine is 2 to 23 $g/cm^2/hr$ (See Reference Example 1), and there have not been obtained preparations which can deliver the drug into the body with satisfactory permeability.

Despite this, the present inventors have found out that, when eptazocine in free form is prepared into an organogel containing a fatty acid ester and a glycerin fatty acid ester, the resulting organogel shows significant skin permeability. On the other hand, when eptazocine hydrobromide which is the same as the active ingredient of commercially available injectable preparations is prepared into the organogel, the resulting organogel has lower skin permeability characteristics than that of the preparation in suspension form described in Non-Patent Document 1 (See Example 1). This reveals that simply applying the drug in liquid form to an organogel does not necessarily provide excellent skin permeability.

Meanwhile, it is found that this pharmaceutical composition for external use in organogel form according to the present invention has excellent skin permeability for not only eptazocine in free form but also other drugs such as tramadol and pentazocine in free form. Further, preparations in matrix or gel form are considered to be generally low in drug release rate of preparations due to the restriction of drug release compared with preparations in liquid form having flowability; however, surprisingly, the pharmaceutical composition for external use according to the present invention shows a very high drug release rate that exceeds that of the preparation in liquid form (See Example 1). This means that little drug remains in the applied composition, which is a highly beneficial feature in preparations in practical use.

PRIOR ART DOCUMENTS

Patent Documents

Patent Document 1: International Publication No. WO2006/085521

Non-Patent Document

Non-Patent Document 1: Proceedings of the 126th Annual Meeting of the Pharmaceutical Society of Japan, Title:

P30[S]am-543 "Effects of caprylic acid monoglyceride on transdermal absorbability of eptazocine"

SUMMARY OF THE INVENTION

Problems to be Solved by the Invention

An object of the present invention is to provide a pharmaceutical composition having excellent skin permeability of drugs and a method for producing the composition.

Solutions to the Problems

The present inventors have obtained findings that skin permeability of drugs such as non-narcotic analgesics is significantly improved by being made in organogel form with a fatty acid ester and a glycerin fatty acid ester, thereby completed the present invention.

The transdermally absorbed pharmaceutical composition for external use according to the present invention can significantly improve skin permeability of drugs such as non-narcotic analgesics, and the composition itself allows a sufficient amount of drug to permeate the skin sustainably, thereby achieving a high therapeutic effect. In particular, the pharmaceutical composition for external use according to the present invention is in a gel form and therefore suitable for being formulated into various dosage forms as preparations for external use, which is highly beneficial in practice. In addition, the pharmaceutical composition for external use according to the present invention has the advantage of providing a very high drug release rate from the preparation (i.e., little drug remains in the applied composition). This is very important for efficient use and management of the drug. Further, the pharmaceutical composition for external use according to the present invention does not release the drug at once as in compositions of a solution or suspension form and does have characteristics capable of releasing the drug sustainably for a long term; therefore, it can be easily applied to a preparation capable of controlling the amount of drug delivery. This is a great advantage when the composition is made into a preparation for the purpose of exhibiting drug efficacy such as analgesia sustainably for a long term.

EMBODIMENTS OF THE INVENTION

Figure 1:
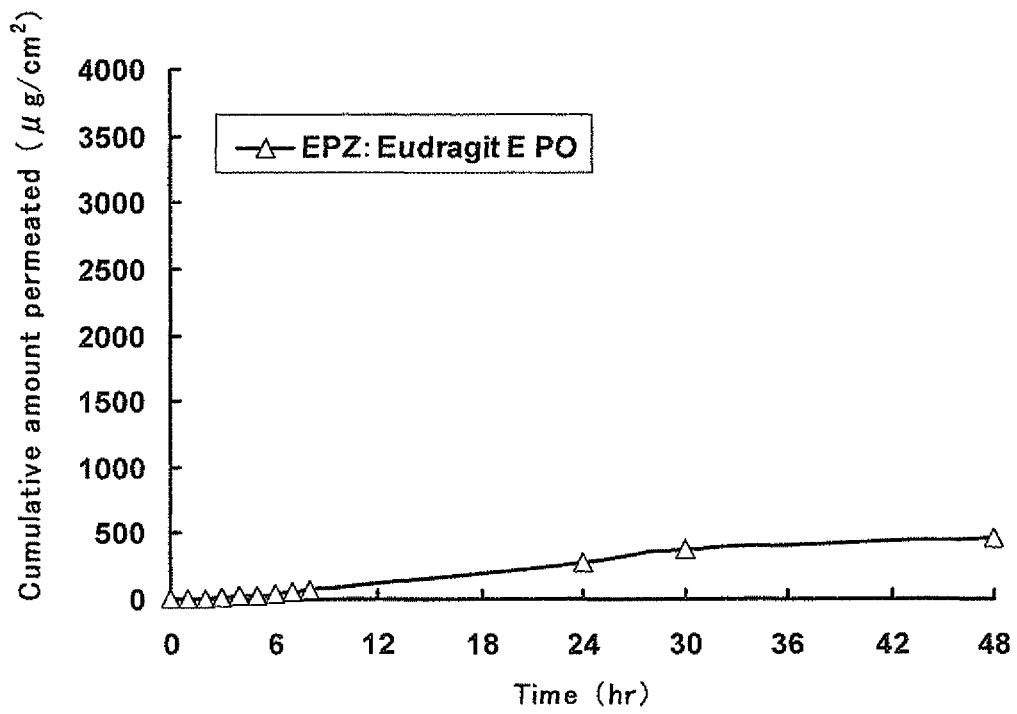
FIG. 1 is a graph showing the cumulative amount of eptazocine permeated through the skin over time in a skin permeation study of an eptazocine-containing matrix-type patch preparation with the use of an acrylic adhesive.

The present invention relates to a pharmaceutical composition for external use which is an organogel containing a fatty acid ester and a glycerin fatty acid ester and a method for producing the composition. Particularly, the present invention relates to a novel transdermally absorbed pharmaceutical composition for external use which has a drug such as non-narcotic analgesics as an active ingredient made in organogel form containing a fatty acid ester and a glycerin fatty acid ester, and a method for producing the composition.

As for the drug used as an active ingredient in the pharmaceutical composition for external use according to the present invention, any types of drugs which are desirably used as preparations for external use can be considered, and one of them is a non-narcotic analgesic. Specific examples thereof include eptazocine, tramadol, pentazocine, buprenorphine and butorphanol, as well as stereoisomers and crystal polymorphisms thereof.

The drug in the present invention could be a salt; however, salts with high hydrophilicity are not appropriate, for example, eptazocine hydrobromide, tramadol hydrochloride and the like are significantly poor in transdermal absorbability compared with those in free form, respectively. In the pharmaceutical composition for external use according to the present invention, drugs such as non-narcotic analgesics can be used alone or in combination appropriately, or can be formulated as a combination preparation with other pharmaceutical active ingredients. The amount of drug to be added varies depending on the type and the dosage form (this will be described later) of the drug, and for example, when the drug is a non-narcotic analgesic, the amount to be added is 0.01 to 20%, preferably 0.05 to 15%, more preferably 0.1 to 10% by weight based on the total weight of the composition.

Examples of the fatty acid ester that can be used in the present invention include a fatty acid ester composed of a fatty acid having 6 to 22 carbon atoms and an alcohol having 1 to 12 carbon atoms. Examples of the fatty acid having 6 to 22 carbon atoms include monocarboxylic acids such as caproic acid, enanthic acid, caprylic acid, capric acid, undecylenic acid, lauric acid, myristic acid, palmitic acid, margaric acid, stearic acid, oleic acid, linoleic acid; and dicarboxylic acids such as adipic acid and sebacic acid. Examples of the alcohol having 1 to 12 carbon atoms include methanol, ethanol, propanol, isopropanol, butanol, tert-butanol, hexanol and octanol. Accordingly, examples of the fatty acid ester include diisopropyl adipate, diethyl sebacate, isopropyl myristate, isopropyl palmitate, isopropyl stearate, butyl stearate, butyl myristate, hexyl laurate, octyl palmitate, ethyl oleate, 2-ethylhexyl palmitate, ethyl stearate and isopropyl linoleate. Preferred examples thereof include isopropyl myristate, isopropyl palmitate, ethyl oleate and isopropyl linoleate, and more preferred among these are isopropyl myristate and isopropyl palmitate. These fatty acid esters may be used alone or two or more kinds thereof may be used in combination. The amount of fatty acid ester to be added is 30 to 95%, preferably 50 to 95% by weight based on the total weight of the composition, although it varies depending on the dosage form which will be described later and the like.

Examples of the glycerin fatty acid ester that can be used in the present invention include a glycerin fatty acid ester having a fatty acid of 5 to 25 carbon atoms. Specific examples thereof include glyceryl caprylate, glyceryl caprate, glyceryl laurate, glyceryl palmitate, glyceryl oleate, glyceryl stearate, glyceryl dicaprylate and glyceryl tricaprylate. Preferred examples thereof include glyceryl monocaprylate, glyceryl monocaprate and glyceryl monolaurate, and more preferred among these are glyceryl monocaprylate and glyceryl monocaprate. These glycerin fatty acid esters may be used alone or two or more kinds thereof may be used in combination. The amount of glycerin fatty acid ester to be added is 1 to 20%, preferably 1 to 15%, more preferably 2 to 10% by weight based on the total weight of the composition, although it varies depending on the dosage form which will be described later and the like.

In the present invention, the organogel refers to a gel whose solvent is an organic solvent among gels, i.e., dispersion systems showing the behavior of an elastic solid rather than a liquid, and it is also called as an oil gel, an oil-based gel and the like.

As for an organogelling agent, although there exist a large number of organogelling agents of high-molecular compounds, an organogelling agent of low-molecular compound type is suitable as the organogelling agent in order to obtain the organogel used in the present invention, and examples thereof include amino acid derivatives such as N-acylamino acid amides, dextrin derivatives such as dextrin fatty acid esters and dibenzylidene sorbitol derivatives. Among them, amino acid derivatives such as N-acylamino acid amides and dextrin derivatives such as dextrin fatty acid esters are suitable. Examples of N-acylamino acid amides include dibutyl lauroyl glutamide [product name: GP-1] and dibutyl ethylhexanoyl glutamide [product name: EB-21], both of which are manufactured by Ajinomoto Co., Inc. Examples of dextrin fatty acid esters include dextrin palmitate [product name: RHEOPEARL KL2, RHEOPEARL KS2, RHEOPEARL TL2], dextrin palmitate/ethylhexanoate [product name: RHEOPEARL TT2] and dextrin myristate [product name: RHEOPEARL MKL2], all of which are manufactured by Chiba Flour Milling Co., Ltd. Examples of dibenzylidene sorbitol derivatives include dibenzylidene sorbitol [product name: GEL ALL D] and methyldibenzylidene sorbitol [product name: GEL ALL MD], both of which are manufactured by New Japan Chemical Co., Ltd. The same kinds of organogelling agents may be used alone or two or more kinds thereof may be used in combination. For example, the combined use of the GP-1 and EB-21 described above makes it possible to adjust the gel strength and transparency appropriately. The amount of organogelling agent to be added is 0.1 to 20%, preferably 1 to 15% by weight based on the total weight of the composition, although it varies depending on the type and the dosage form (this will be described later) of the used gelling agent.

The pharmaceutical composition for external use according to the present invention can be produced by mixing the drug, the fatty acid ester, the glycerin fatty acid ester and the organogelling agent. Commonly performed or recommended methods with the use of the organogelling agent can be employed, and other appropriate solvents such as lower alcohols (alcohols having 1 to 4 carbon atoms, e.g. ethanol, methanol and isopropyl alcohol), ethyl acetate, organic acids (fatty acids having 6 to 22 carbon atoms, e.g. myristic acid and oleic acid) can be used as needed, in order to uniformly dissolve or disperse the drug or other components in the preparation. The mixed solution is subjected to conditions suitable for each organogelling agent, such as heating followed by cooling to form a gel, so that it can be formed into a final organogel.

As for the drug, as mentioned above, non-narcotic analgesics and any other types of drugs which are desirably used as preparations for external use can be considered. Eptazocine, tramadol and pentazocine are suitable when being in free form. As for drugs which are in a suspension state in the organogel composition such as in particular eptazocine, before addition of an organogelling agent, eptazocine is added to an appropriate amount of components other than the organogelling agent (a fatty acid ester, or a fatty acid ester and a glycerin fatty acid ester), and then these are mixed while grinding eptazocine, thereby the obtained composition is further improved in transdermal absorbability of the drug.

Various preparations for external use can be produced by using the pharmaceutical composition for external use according to the present invention. That is, it is possible to produce desired preparations for external use by combining a base, an adjuvant, an additive and the like as needed, according to commonly used methods described in General Rules for Preparations of Japanese Pharmacopoeia and the like or methods suitable for various organogelling agents.

The dosage form of the pharmaceutical composition for external use according to the present invention is not particularly limited, and the pharmaceutical composition for external use according to the present invention can be formulated into various preparations for external use which allows drugs to be absorbed through the skin, such as patch, gel, ointment and cream preparations. For example, the patch preparation can be made as a reservoir-type transdermally absorbed patch preparation in which the pharmaceutical composition for external use according to the present invention is enclosed or a matrix-type transdermally absorbed patch preparation in which an adhesive is added to the pharmaceutical composition for external use according to the present invention. In particular, the pharmaceutical composition for external use according to the present invention is suitable to be formulated into a patch preparation and thereby made as a sustained-release preparation that can control the release of drugs. Examples of the sustained-release preparation include a type of sustained-release preparation to be applied once per day and a type of sustained-release preparation to be applied once per two days.

The reservoir-type patch preparation has a drug reservoir. In general, the drug reservoir is covered with a support at the outer side and covered with a drug release membrane (drug control membrane) at the skin side. The influence on the skin permeability of drugs is given by the drug release membrane, and it is confirmed that in the pharmaceutical composition for external use according to the present invention, drugs in the gel are transdermally absorbed through a membrane such as a porous polypropylene membrane, a nitrocellulose membrane and a membrane filter composed of a tetrafluoroethylene resin and the like. Accordingly, the pharmaceutical composition for external use according to the present invention can be formulated into reservoir-type preparations with the use of various drug release membranes.

The matrix-type patch preparation has a support (backing) and an adhesive base layer. In general, drugs are included in this adhesive base layer. Examples of the adhesive in the adhesive base include acrylic resins (e.g., aminoalkyl methacrylate copolymers and methacrylic acid copolymers), silicone resins, styrene isoprene block copolymers, aliphatic hydrocarbon resins (petroleum resins obtained by polymerizing unsaturated monomers extracted from C5 fraction), alicyclic saturated hydrocarbon resins, terpene resins (e.g., hydrogenated terpene resins), rosin ester resins (e.g., hydrogenated rosin ester resins), polyisobutylene resins and the like, and they may be used alone or two or more kinds thereof may be used in combination. The adhesive base is prepared by adding the adhesive to a drug-containing organogel. This adhesive base can be laminated on a support (backing) by a commonly used method such as a coating method and a casting method to produce a matrix-type patch preparation.

Moreover, the gel preparation can be made as a wide variety of preparations differing in their hardness and viscosity, including from a gel preparation almost like a liquid preparation with slight viscosity to a stick-type hard gel preparation, as well as an O/W emulsion cream preparation. The composition suitable for these preparations can be produced by adjusting the type and the concentration of the organogelling agent appropriately.

EXAMPLE

Hereinafter, the present invention will be explained in detail with reference to examples and references; however, it is not limited to these. It is to be noted that all of % in examples refer to % by weight unless specified otherwise. Hereinafter, the drugs eptazocine, tramadol, pentazocine and the like refer to those in their free from, unless specified that they are in their salt form. It is to be noted that, hereinafter, abbreviations may be used, eptazocine as EPZ, tramadol as TRD, and pentazocine as PTZ.

Reference 1. Matrix-Type Patch Preparation
1. Preparation of Acrylic Adhesive
First, 21.0 g of acetone, 11.7 g of ethanol and 2.3 g of 2-propanol were weighed into a beaker and stirred to mix uniformly. Then, 42.2 g of aminoalkyl methacrylate copolymer E (EUDRAGIT E PO, manufactured by Evonik Degussa Japan Co., Ltd.) was added thereto gradually while stirring to dissolve. Thereafter, 19.0 g of dibutyl sebacate, which is a plasticizer, was added promptly and stirred for 10 minutes. Lastly, 3.8 g of succinic acid, which is a cross-linking agent, was added gradually while stirring to dissolve solid components completely, so that an EUDRAGIT E adhesive (solid component content 65%) was obtained.

2. Preparation of Patch Preparation
First, 49.99 mg (10%) of eptazocine (EPZ), 50.21 mg (10%) of isopropyl myristate (IPM) and 24.64 mg (5%) of glyceryl monocaprylate (GEFA-$C_8$) were weighed into a sample tube respectively, and a small amount of acetone or methanol was added to dissolve the mixture. Next, 600.8 mg of the EUDRAGIT E adhesive (solid component 390.5 mg) described above was added thereto and mixed while stirring. This solution was coated onto a support (SCOTCHPAK 9732 Backing, manufactured by 3M Health Care Limited) which had been fixed on a flat glass plate, at a thickness of 200 μm with the use of a film applicator. Then, the coated support was dried at 60° C. for 20 minutes in a forced air flowoven. Thereafter, the fluororesin-coated surface of a detachable film (SCOTCHPAK 1022 Release Liner, manufactured by 3M Health Care Limited) was bonded to the adhesion surface of the preparation, to give a 10% EPZ-containing patch preparation.

In addition, matrix-type patch preparations were produced in the same manner as described above, except that, in place of EUDRAGIT E PO, there was used an EUDRAGIT RS/RL (1:4) adhesive of EUDRAGIT RS PO and EUDRAGIT RL PO mixed at a ratio of 1:4, an EUDRAGIT RS/RL (1:1) adhesive of EUDRAGIT RS PO and EUDRAGIT RL PO mixed at a ratio of 1:1, or other type of acrylic adhesive DURO-TAK 87-9301 or DURO-TAK 87-2677 (manufactured by Henkel Japan Ltd.). The formulation of the produced matrix-type patch preparations is shown in Table 1.

TABLE 1

| Matrix-type patch preparation No. | Acrylic adhesive | EPZ (%) | IPM (%) | GEFA-$C_8$ (%) |
|---|---|---|---|---|
| 1 | Eudragit E PO | 10 | 10 | 5 |
| 2 | Eudragit E PO | 20 | 10 | 5 |
| 3 | Eudragit RS/RL (1:4) | 10 | 10 | 5 |
| 4 | Eudragit RS/RL (1:1) | 10 | 10 | 5 |
| 5 | Duro-Tak 87-9301 | 10 | 10 | 5 |
| 6 | Duro-Tak 87-2677 | 5 | 10 | 5 |

3. Skin Permeation Studies
The excised skin of a male hairless mouse (4 to 7 weeks of age) was set between a receptor phase and a donor phase of a Franz diffusion cell, and the receptor phase was filled with McIlvain buffer (pH 4.2). The rotation speed of a stirrer was about 650 rpm, and the experimental temperature was 32° C. The various patch preparations were cut into circles of 12 mm in diameter, and each of which was applied onto the skin (donor phase) which had been immersed in the McIlvain buffer for 1 hour in advance. The time of starting the application was regarded as 0 hour, and every 1 hour from 0 to 8 hours and at 24 hours, 30 hours and 48 hours from the time of starting the application, sampling was carried out manually. The sampling was carried out by adding 0.5 ml of the buffer which had been kept at 32° C. to the receptor phase of the Franz diffusion cell and removing the same amount of the sample therefrom. The collected sample was quantitatively determined with high-performance liquid chromatography (HPLC), so that the amount of EPZ that permeated the skin (n=4) was obtained.

[HPLC Conditions]
Detector: Ultraviolet-visible detector (measurement wavelength: 278 nm)
Column: Inertsil ODS-3 (φ4.6 mm×150 mm)
Flow rate: 1.0 mL/min Column temperature: room temperature
Mobile phase: 50 mM phosphate-buffered aqueous solution: acetonitrile=85:15
Injection amount of sample: 10 μL
(The drug concentration of the standard solution was prepared as 0.2 mg/mL, and the drug concentration of each sample was calculated by the absolute calibration method.)

The permeation rate (flux) and the lag time were calculated from the amount of EPZ that permeated the skin of each matrix-type patch preparation. They are shown in Table 2 together with the cumulative amount permeated (after 48 hours). In addition, a graph of the cumulative amount permeated over time of the matrix-type patch preparation No. 1 is shown in FIG. 1. In the present invention, a regression line was determined from cumulative amounts permeated at not less than four measurement times (three measurement times depending on circumstances) to give its maximum value of the slope of the regression line as the permeation rate (flux), and moreover the x-intercept of the regression line was determined to give its value as the lag time.

TABLE 2

| Matrix-type patch preparation No. | Permeation rate (μg/cm$^2$/hr) | Lag time (hr) | Cumulative amount permeated (after 48 hours) (μg/cm$^2$) |
|---|---|---|---|
| 1 | 14.2 ± 2.0 | 2.8 ± 0.2 | 457.0 ± 77.5 |
| 2 | 22.5 ± 0.8 | 3.6 ± 0.9 | 503.2 ± 47.4 |
| 3 | 7.4 ± 3.2 | 15.2 ± 1.0 | 243.8 ± 110.3 |
| 4 | 7.4 ± 1.4 | 7.7 ± 3.9 | 304.0 ± 55.8 |
| 5 | 3.0 ± 0.3 | 8.0 ± 0.5 | 123.8 ± 12.1 |
| 6 | 2.6 ± 0.3 | 6.3 ± 1.3 | 103.6 ± 10.4 |

Example 1

Comparison Between Suspension and Organogel

1. Preparation of Each Sample
(1) Eptazocine-Containing GP-1 Organogel

Into a test tube were added 63.56 mg of EPZ (2%), 124.73 mg of GP-1 (4%) and 153.47 mg of GEFA-C$_8$ (5%) and further added 2677.55 mg of IPM to give a total amount of 3019.31 mg. The test tube was placed in a heating block which had been heated at 130° C. to heat the mixture solution. The test tube was occasionally taken out of the heating block and stirred with a vortex mixer to dissolve GP-1 uniformly. After GP-1 was dissolved, the heating block was set to a temperature of 80° C., and the resulting solution was cooled while stirring occasionally to mix uniformly. When the solution was cooled to 90° C. or less, it was taken out of the heating block and allowed to cool while stirring, so that an EPZ-containing organogel was obtained.

Into a test tube were added 84.42 mg of eptazocine hydrobromide (EPZ HBr) (2% as EPZ), 120.85 mg of GP-1 (4%) and 147.96 mg of GEFA-C$_8$ (5%) and further added 2632.08 mg of IPM to give a total amount of 2985.31 mg. Thereafter, an EPZ.HBR-containing organogel was prepared in the same manner as in the above 1.(1).

(3) Eptazocine-Containing Suspension
Into a test tube were added 18.43 mg of EPZ (0.6%) and 156.84 mg of GEFA-C$_8$ (5%) and further added IPM to give a total amount of 3000 mg. The mixed solution was stirred well and then dispersed uniformly with ultrasonic treatment for 20 minutes to give an EPZ suspension.

(4) Eptazocine Hydrobromide-Containing Suspension
Into a test tube were added 24.82 mg of EPZ HBr (0.6% as EPZ) and 149.60 mg of GEFA-C$_8$ (5%) and further added IPM to give a total amount of 3000 mg. Thereafter, an EPZ.HBr suspension was prepared in the same manner as in the above 1.(3).

2. Mouse Skin Permeation Studies
(1) Mouse Skin Permeation Studies of Organogel

The excised skin of a male hairless mouse (4 to 7 weeks of age) was set between a receptor phase and a donor phase of a Franz diffusion cell, and the receptor phase was filled with McIlvain buffer. The rotation speed of a stirrer was about 650 rpm, and the experimental temperature was 32° C. Each organogel prepared in 1. (1) and (2) described above was applied in an amount of about 280 mg onto the skin (donor phase) which had been immersed in with the McIlvain buffer for 1 hour in advance. The time of starting the application was regarded as 0 hour, and every 1 hour from 0 to 8 hours and every 4 hours from 8 to 48 hours, sampling was carried out with an automatic sampling system (product name: Microette Plus, manufactured by Hanson Research Corporation). The sampling was carried out by removing 2.0 mL of a sample from the receptor phase of the Franz diffusion cell and supplementing this with the same amount of the buffer which had been kept at 32° C. The collected sample was quantitatively determined with high-performance liquid chromatography (HPLC), so that the amount of EPZ that permeated the skin (n=5) was obtained. Here, the HPLC conditions were the same as those in Reference 1 described above.

(2) Mouse Skin Permeation Studies of Suspension

In the same manner as in the above 2.(1), the EPZ-containing suspension and the EPZ.HBr-containing suspension prepared in the above 1.(3) and (4) were each applied in an amount of 1 mL (specific gravity: about 0.85), and the mouse skin permeation studies were carried out.

Figure 2:
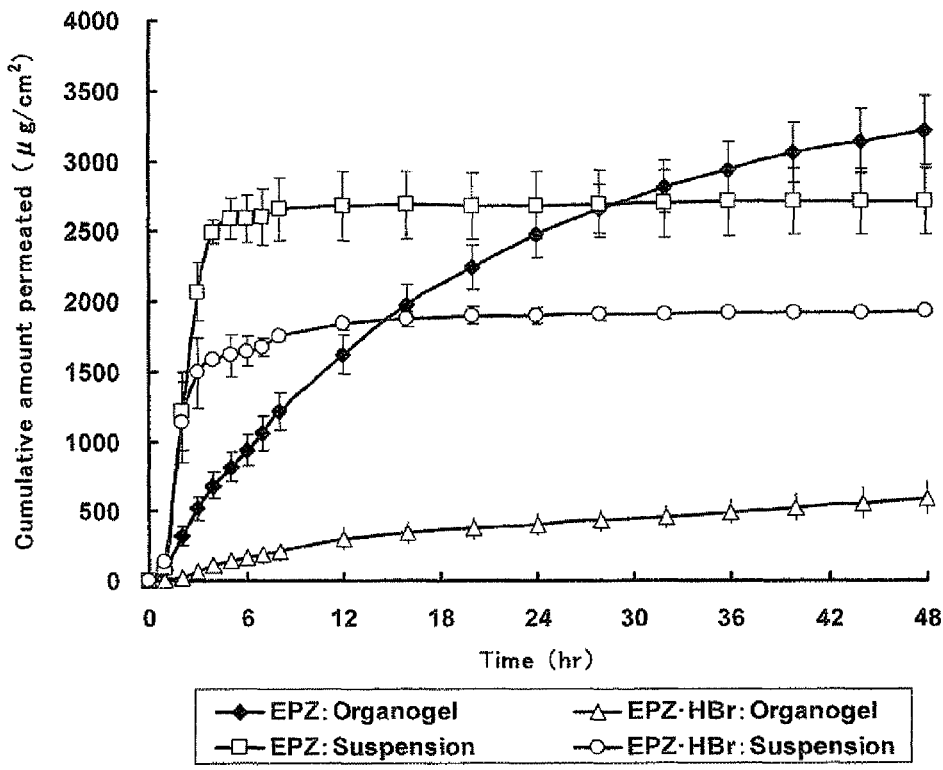
FIG. 2 is a graph showing results obtained by comparing the cumulative amount of eptazocine permeated through the skin of each sample over time in a skin permeation study of an eptazocine-containing GP-1 organogel (as just described, hereinafter, the pharmaceutical composition for external use according to the present invention may be sometimes called as an organogel prefixed with the names of a contained drug and an used organogelling agent; and note that GP-1 will be described later), an eptazocine hydrobromide-containing GP-1 organogel, an eptazocine-containing suspension or an eptazocine hydrobromide-containing suspension.

As for the four compositions prepared in the above 1.(1) to (4) in Example 1, the permeation rate and the lag time were calculated from each amount of EPZ that permeated the skin measured in the above 2.(1) and (2). They are shown in Table 3 together with the cumulative amount permeated (after 48 hours). In addition, a graph of the cumulative amount permeated over time of each EPZ-containing organogel and suspension is shown in FIG. 2. Moreover, "Drug release rate from the preparation", which is obtained by dividing the applied amount of drug by the released amount of drug (after 48 hours), is shown in Table 4.

TABLE 3

| Example 1 No. | Sample | Permeation rate (μg/cm$^2$/hr) | Lag time (hr) | Cumulative amount permeated (after 48 hours) (μg/cm$^2$) |
|---|---|---|---|---|
| 1 | (1) EPZ-containing organogel | 201.8 | 0.5 | 3218.9 |
| | (2) EPZ•HBr-containing organogel | 39.9 | 1.49 | 596.5 |
| | (3) EPZ suspension | 806.4 | 1.1 | 2712.4 |
| | (4) EPZ•HBr suspension | 509.6 | 0.3 | 1929.0 |

TABLE 4

| Example 1 No. | Smaple | Applied amount of drug (µg) | Released amount of drug (after 48 hours) (µg) | Drug release rate from the preparation (%) |
|---|---|---|---|---|
| 1 | (1) EPZ-containing organogel | 5954 | 5688 | 95.6 |
|  | (2) EPZ•HBr-containing organogel | 5925 | 1054 | 17.8 |
|  | (3) EPZ suspension | 5222 | 4793 | 91.8 |
|  | (4) EPZ•HBr suspension | 5210 | 3409 | 65.4 |

Example 2

Preparation of Organogel

1. Preparation of Eptazocine-Containing Organogel (1) Eptazocine-Containing GP-1 Organogel (First Method)

Into a test tube were added 60.52 mg of EPZ (2%), 121.1 mg of GP-1 (4%) and 151.5 mg of GEFA-$C_8$ (5%) and further added IPM to give a total amount of 3000.8 mg. The test tube was placed in a heating block which had been heated at 130° C. to heat the mixture solution. The test tube was occasionally taken out of the heating block and stirred to dissolve GP-1 uniformly. After GP-1 was dissolved, the heating block was set to a temperature of 80° C., and the solution was cooled while stirring occasionally to disperse the drug uniformly. When the solution was cooled to about 90° C., it was taken out of the heating block and allowed to cool while stirring, so that an organogel was obtained.

(2) Eptazocine-Containing GP-1 Organogel (Second Method)

First, 100.53 mg of EPZ, 251.6 mg of GEFA-$C_8$ and 2011.9 mg of IPM were taken and then mixed while grinding EPZ in a mortar to give an EPZ suspension. Into a test tube were added 1912.4 mg of this suspension [content: EPZ 81.32 mg (2%), GEFA-$C_8$ 203.5 mg (5%)] and 160.1 mg of GP-1 (4%) and further added IPM to give a total amount of 4021.2 mg. The test tube was placed in a heating block which had been heated at 130° C. to heat the mixture solution. The test tube was occasionally taken out of the heating block and stirred to dissolve GP-1 uniformly. After GP-1 was dissolved, the heating block was set to a temperature of 90° C., and the solution was cooled while stirring occasionally to disperse the drug uniformly. When the solution was cooled to about 100° C., it was taken out of the heating block and stirred slowly until it started to turn into a gel. The stirring was stopped when the solution started to turn into a gel, and this was allowed to stand, so that an organogel was obtained.

(3) Eptazocine-Containing EB-21 Organogel (First Method)

Into a test tube were added 60.20 mg of EPZ (2%), 121.5 mg of EB-21 (4%) and 153.9 mg of GEFA-$C_8$ (5%) and further added IPM to give a total amount of 2999.3 mg. The test tube was placed in a heating block which had been heated at 140° C. to heat the mixture solution. The test tube was occasionally taken out of the heating block and stirred to dissolve EB-21 uniformly. After EB-21 was dissolved, the heating block was set to a temperature of 100° C., and the solution was cooled while stirring occasionally to mix uniformly. When the solution was cooled to 120° C. or less, it was taken out of the heating block and allowed to cool while stirring, so that an organogel was obtained.

(4) Eptazocine-Containing EB-21 Organogel (Second Method)

First, 100.11 mg of EPZ, 250.9 mg of GEFA-$C_8$ and 2151.3 mg of IPM were taken and then mixed while grinding EPZ in a mortar to give an EPZ suspension. Into a test tube were added 2009.7 mg of this suspension [content: EPZ 80.40 mg (2%), GEFA-$C_8$ 201.5 mg (5%)] and 160.0 mg of EB-21 (4%) and further added IPM to give a total amount of 4000.1 mg. The test tube was placed in a heating block which had been heated at 140° C. to heat the mixture solution. The test tube was occasionally taken out of the heating block and stirred to dissolve EB-21 uniformly. After EB-21 was dissolved, the heating block was set to a temperature of 100° C., and the solution was cooled while stirring occasionally to disperse the drug uniformly. When the solution was cooled to about 120° C., it was taken out of the heating block and stirred slowly until it started to turn into a gel. The stirring was stopped when the solution started to turn into a gel, and this was allowed to stand, so that an organogel was obtained.

(5) Eptazocine-Containing GP-1 and EB-21 Organogel (Combined Use of GP-1 and EB-21)

Into a test tube were added 60.03 mg of EPZ (2%), 89.7 mg of GP-1 (3%), 30.7 mg of EB-21 (1%) and 150.8 mg of GEFA-$C_8$ (5%) and further added IPM to give a total amount of 3004.5 mg. The test tube was placed in a heating block which had been heated at 130° C. to heat the mixture solution. The test tube was occasionally taken out of the heating block and stirred with a vortex mixer to dissolve GP-1 and EB-21 uniformly. After GP-1 and EB-21 were dissolved, the heating block was set to a temperature of 80° C., and the solution was cooled while stirring occasionally to mix uniformly. When the solution was cooled to 90° C. or less, it was taken out of the heating block and allowed to cool while stirring, so that an organogel was obtained.

(6) Eptazocine-Containing RHEOPEARL KL2 Organogel

Into a test tube were added 59.76 mg of EPZ (2%), 298.8 mg of RHEOPEARL KL2 (10%) and 153.4 mg of GEFA-$C_8$ (5%) and further added IPM to give a total amount of 3002.9 mg. The test tube was placed in a heating block which had been heated at 95° C. to heat the mixture solution. The test tube was occasionally taken out of the heating block and stirred with a vortex mixer to dissolve RHEOPEARL KL2 uniformly. After RHEOPEARL KL2 was dissolved, the resulting solution was taken out of the heating block and allowed to cool while stirring, so that an organogel was obtained.

(7) Eptazocine-Containing RHEOPEARL KS2 Organogel

Into a test tube were added 60.20 mg of EPZ (2%), 297.7 mg of RHEOPEARL KS2 (10%) and 153.2 mg of GEFA-$C_8$ (5%) and further added IPM to give a total amount of 3005.8 mg. Thereafter, an organogel was prepared in the same manner as in the above 1.(6).

2. Preparation of Tramadol-Containing Organogel (1) Tramadol-Containing GP-1 Organogel Into a test tube were added 60.76 mg of tramadol (TRD) (2%), 150.4 mg of GEFA-$C_8$ (5%) and 120.8 mg of GP-1 (4%) and further added IPM to give a total amount of 3007.2 mg.

The test tube was placed in a heating block which had been heated at 135° C. to heat the mixture solution. The test tube was occasionally taken out of the heating block and stirred to dissolve the mixture solution uniformly. After the solution was mixed uniformly, the heating block was set to a temperature of 90 C, and the solution was stirred occasionally. When the solution was cooled to 100° C. or less, it was taken out of the heating block and stirred slowly at room temperature until it started to turn into a gel. The stirring was stopped when the solution started to turn into a gel, and this was allowed to stand, so that an organogel was obtained.

(2) Tramadol Hydrochloride-Containing GP-1 Organogel

First, 91.23 mg of tramadol hydrochloride (TRD.HCl) (2% as TRD), 199.0 mg of GEFA-$C_8$ and 1602.4 mg of IPM were taken and then mixed while grinding TRD.HCl in a mortar to give a TRD.HCl suspension. Into a test tube were added 1438.1 mg of this suspension (content: TRD.HCl 69.32 mg [60.89 mg as TRD](2%), GEFA-$C_8$ 151.2 mg (5%)) and 121.3 mg of GP-1 (4%) and further added IPM to give a total amount of 3020.0 mg. The test tube was placed in a heating block which had been heated at 135° C. to heat the mixture solution. The test tube was occasionally taken out of the heating block and stirred to dissolve GP-1 uniformly. After GP-1 was dissolved, the heating block was set to a temperature of 90° C., and the solution was cooled while stirring occasionally to disperse the drug uniformly. When the solution was cooled to about 105° C., it was taken out of the heating block and stirred slowly at room temperature until it started to turn into a gel. The stirring was stopped when the solution started to turn into a gel, and this was allowed to stand, so that an organogel was obtained.

3. Preparation of Pentazocine-Containing Organogel (1) Pentazocine-Containing GP-1 Organogel Into a test tube were added 79.86 mg of pentazocine (PTZ) (2%), 204.0 mg of GEFA-$C_8$ (5%) and 162.7 mg of GP-1 (4%) and further added IPM to give a total amount of 3998.3 mg. The test tube was placed in a heating block which had been heated at 135° C. to heat the mixture solution. The test tube was occasionally taken out of the heating block and stirred to dissolve the mixture solution uniformly. After the solution was mixed uniformly, the heating block was set to a temperature of 90° C., and the solution was stirred occasionally. When the solution was cooled to 100° C. or less, it was taken out of the heating block and stirred slowly at room temperature until it started to turn into a gel. The stirring was stopped when the solution started to turn into a gel, and this was allowed to stand, so that an organogel was obtained.

Example 3

Mouse Skin Permeation Studies of Organogel (1) Mouse Skin Permeation Studies of Eptazocine-Containing Organogel The excised skin of a male hairless mouse (4 to 9 weeks of age) was set between a receptor phase and a donor phase of a Franz diffusion cell, and the receptor phase was filled with McIlvain buffer (pH 4.2). The rotation speed of a stirrer was about 650 rpm, and the experimental temperature was 32° C. Each EPZ-containing organogel prepared in the above 1. in Example 2 was applied in an amount of about 300 mg onto the skin (donor phase) which had been immersed in the McIlvain buffer for 1 hour in advance. The time of starting the application was regarded as 0 hour, and every 1 hour from 0 to 8 hours and every 2 hours from 20 to 30 hours and from 44 to 48 hours, sampling was carried out manually. The sampling was carried out by adding 0.5 mL of the McIlvain buffer which had been kept at 32° C. to the receptor phase of the Franz diffusion cell and removing the same amount of the sample therefrom. The collected sample was quantitatively determined with high-performance liquid chromatography (HPLC), so that the amount of EPZ that permeated the skin (n=4) was obtained. Here, the HPLC conditions were the same as those in Reference 1 described above.

(2) Mouse Skin Permeation Studies of Tramadol-Containing Organogel

As for the TRD (in free or hydrochloride form)-containing organogels prepared in the above 2. in Example 2, the amount of TRD that permeated the skin (n=4) was obtained in the same manner as in the above (1).

[HPLC Conditions]

Detector: Ultraviolet-visible detector (measurement wavelength: 271 nm)

Column: Inertsil ODS-3 (φ4.6 mm×150 mm)

Flow rate: 1.0 mL/min

Column temperature: 40° C.

Mobile phase: trifluoroacetic acid-buffered aqueous solution (1→2000):acetonitrile=80:20

Injection amount of sample: 10 μL (The drug concentration of the standard solution was prepared as 0.25 mg/mL, and the drug concentration of each sample was calculated by the absolute calibration method.)

(3) Mouse Skin Permeation Studies of Pentazocine-Containing Organogel

In the same manner as in the above (1) except that PBS buffer (phosphate buffered saline) (pH 7.5) was used in the receptor phase, the PTZ-containing organogel prepared in the above 3. in Example 2 was applied in an amount of about 300 mg, and the amount of PTZ that permeated the skin (n=4) was obtained.

[HPLC Conditions]

Detector: Ultraviolet-visible detector (measurement wavelength: 278 nm)

Column: Capcell pak C18 (φ4.6 mm×150 mm)

Flow rate: 1.0 mL/min

Column temperature: room temperature

Mobile phase: 50 mM phosphate-buffered aqueous solution: acetonitrile=77:23

Injection amount of sample: 10 μL (The drug concentration of the standard solution was prepared as 0.1 mg/mL, and the drug concentration of each sample was calculated by the absolute calibration method.)

As for the ten compositions prepared in the above 1. to 3. in Example 2, the permeation rate and the lag time were calculated from the amount of drug that permeated the skin measured in the above (1) to (3) in Example 3. They are shown in Table 5 together with the cumulative amount permeated (after 48 hours). In addition, graphs of the cumulative amount permeated over time of these drug-containing organogels are shown in FIGS. 3 to 8, respectively. It is to be noted that, as for PTZ, an organogel of EB-21 (4%) in place of GP-1 (4%) was prepared and the skin permeation studies were carried out, the result of which showed the skin permeability (permeation rate, lag time, cumulative amount permeated) approximately same as that in the case of GP-1.

TABLE 5

Figure 3:
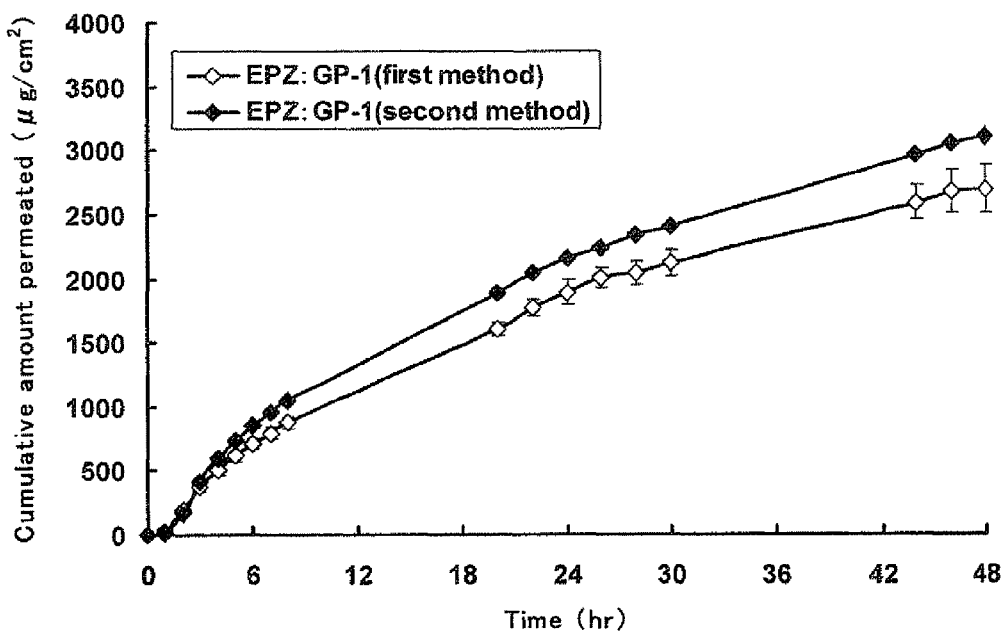
FIG. 3 is a graph showing the cumulative amount of eptazocine permeated through the skin over time in a skin permeation study of eptazocine-containing GP-1 organogels prepared in different methods.
Figure 4:
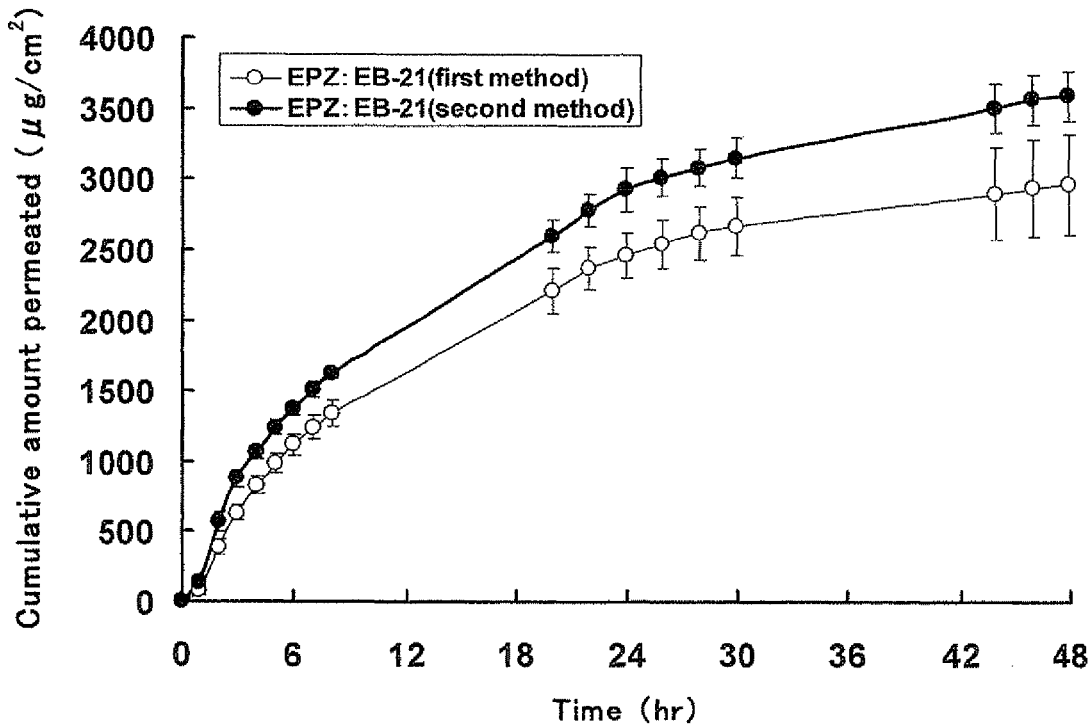
FIG. 4 is a graph showing the cumulative amount of eptazocine permeated through the skin over time in a skin permeation study of eptazocine-containing EB-21 organogels prepared in different methods (Note that EB-21 will be described later).
Figure 5:
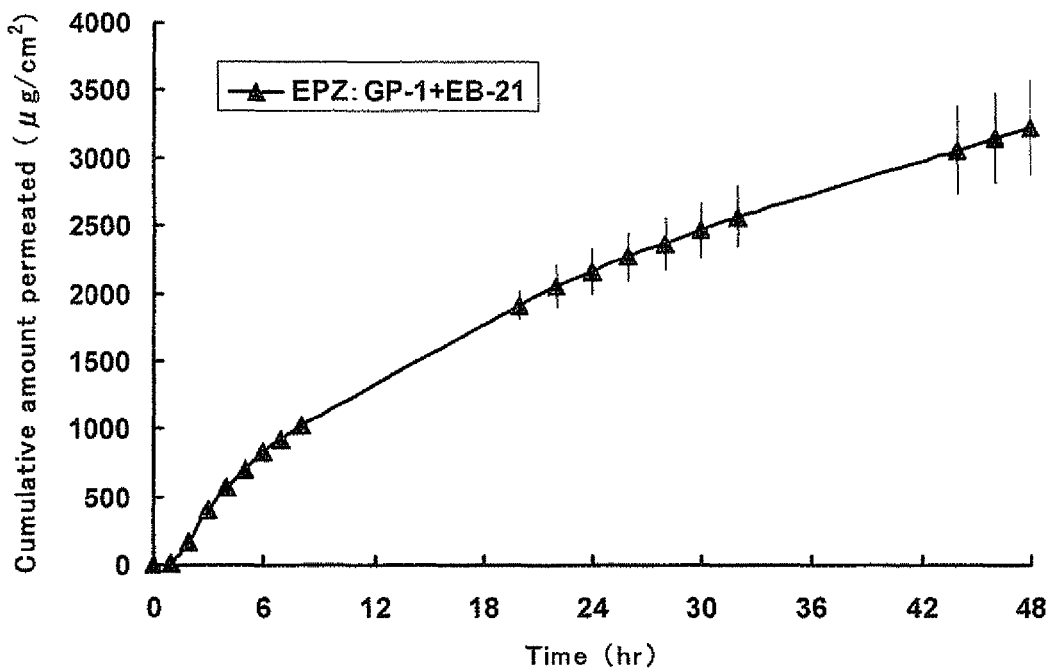
FIG. 5 is a graph showing the cumulative amount of eptazocine permeated through the skin over time in a skin permeation study of an eptazocine-containing GP-1 and EB-21 organogel (combined use of GP-1 and EB-21).
Figure 6:
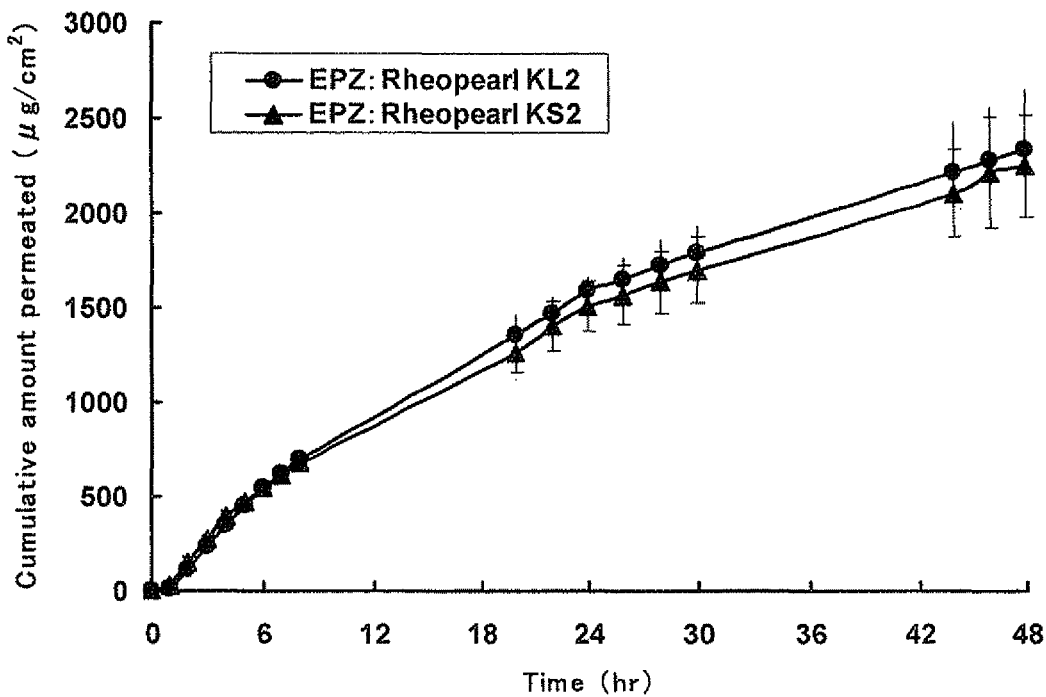
FIG. 6 is a graph showing the cumulative amount of eptazocine permeated through the skin over time in a skin permeation study of an eptazocine-containing RHEOPEARL KL2 organogel or an eptazocine-containing RHEOPEARL KS2 organogel (Note that RHEOPEARL KL2 and RHEOPEARL KS2 will be described later).
Figure 7:
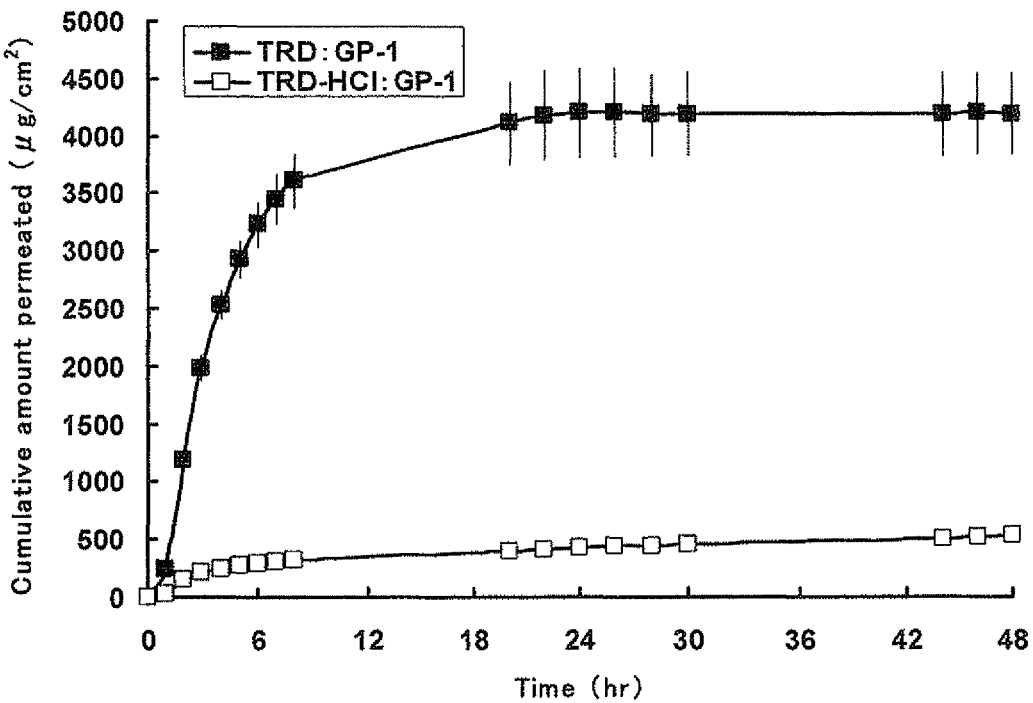
FIG. 7 is a graph showing results obtained by comparing the cumulative amount of tramadol permeated through the skin over time in a skin permeation study of a tramadol-containing GP-1 organogel or a tramadol hydrochloride-containing GP-1 organogel.
Figure 8:
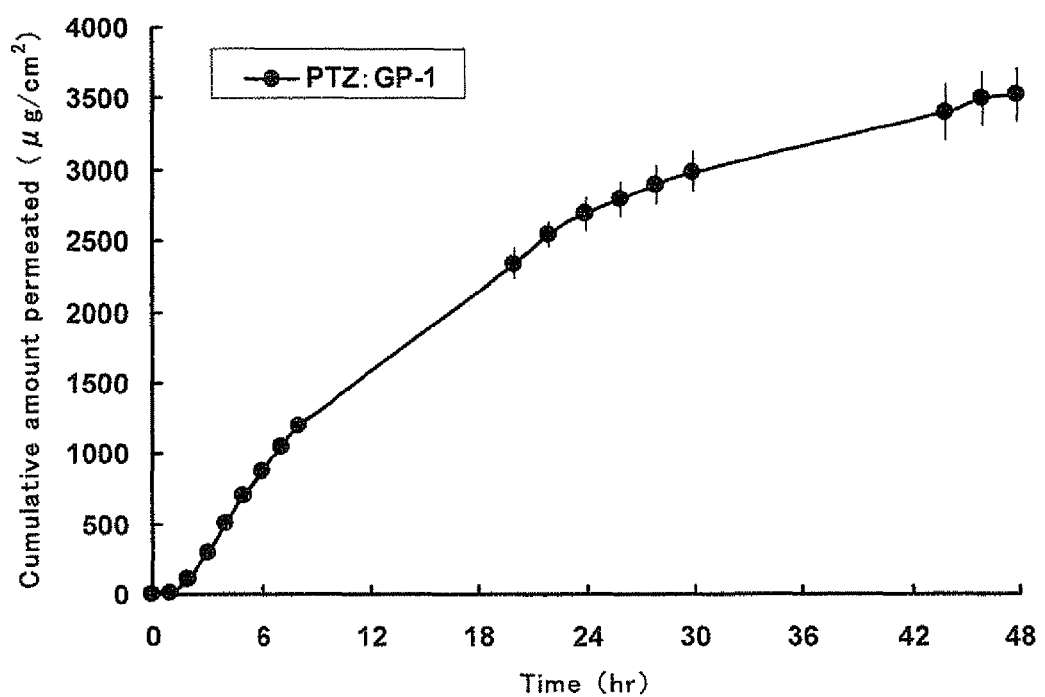
FIG. 8 is a graph showing the cumulative amount of pentazocine permeated through the skin over time in a skin permeation study of a pentazocine-containing GP-1 organogel.

| Example 2 No. | | Organogel | Permeation rate (μg/cm²/hr) | Lag time (hr) | Cumulative amount permeated (after 48 hours) (μg/cm²) | Graph of Cumulative amount permeated |
|---|---|---|---|---|---|---|
| 1 | (1) | EPZ GP-1 (first method) | 161.5 ± 9.9 | 0.8 ± 0.1 | 2698.9 ± 188.5 | FIG. 3 |
|   | (2) | GP-1 (second method) | 199.6 ± 10.6 | 1.0 ± 0.1 | 3109.9 ± 80.4 |  |
|   | (3) | EB-21 (first method) | 250.5 ± 15.4 | 0.6 ± 0.2 | 2968.5 ± 359.0 | FIG. 4 |
|   | (4) | EB-21 (second method) | 310.1 ± 4.7 | 0.4 ± 0.2 | 3594.7 ± 177.8 |  |
|   | (5) | GP-1 + EB-21 | 191.0 ± 8.6 | 1.0 ± 0.06 | 3226.5 ± 351.0 | FIG. 5 |
|   | (6) | Rheopearl KL2 | 114.7 ± 5.2 | 0.9 ± 0.1 | 2343.3 ± 305.9 | FIG. 6 |
|   | (7) | Rheopearl KS2 | 122.6 ± 8.2 | 0.8 ± 0.2 | 2250.8 ± 268.1 |  |
| 2 | (1) | TRD GP-1 | 765.1 ± 45.8 | 0.6 ± 0.1 | 4195.2 ± 355.6 | FIG. 7 |
|   | (2) | TRD-HCl GP-1 | 75.6 ± 9.6 | 0.2 ± 0.1 | 527.0 ± 14.6 |  |
| 3 | (1) | PTZ GP-1 | 198.1 ± 5.0 | 1.5 ± 0.1 | 3532.4 ± 184.0 | FIG. 8 |

Example 4

Skin Permeability of Organogels in which Various Fatty Acid Esters are Used

Figure 9:
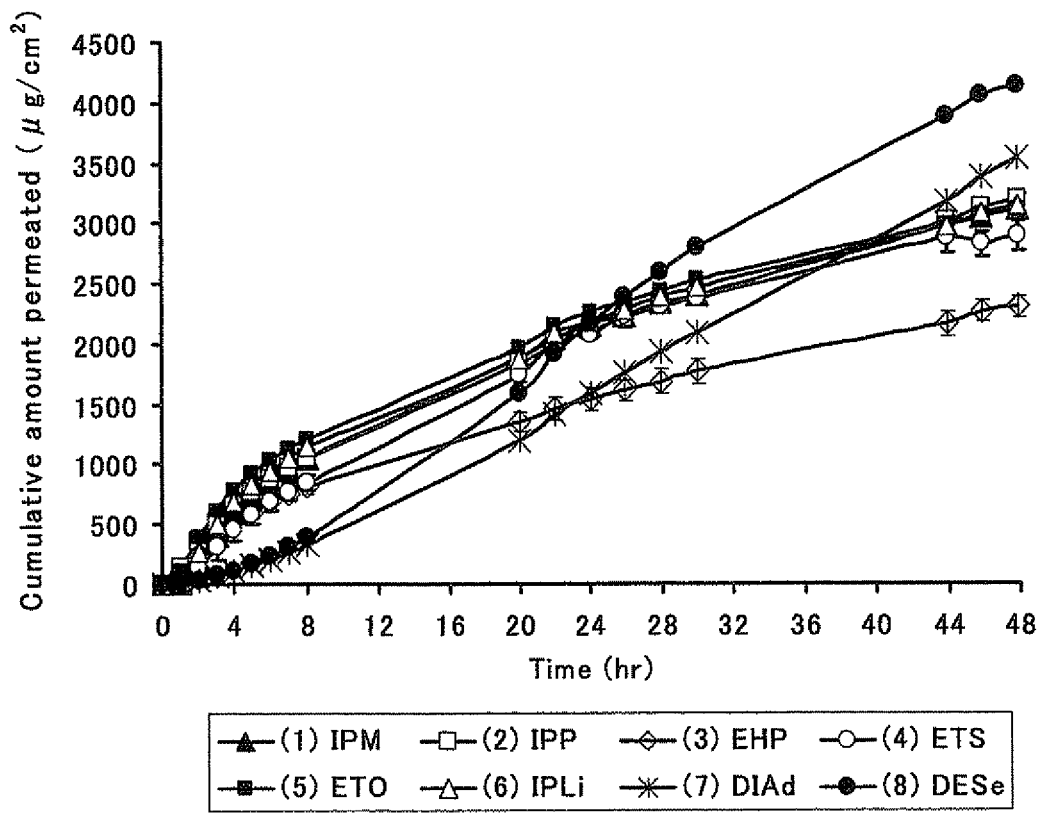
FIG. 9 is a graph showing the cumulative amount of eptazocine permeated through the skin over time in a skin permeation study of eptazocine-containing GP-1 organogels in which various fatty acid esters are used.

1. Preparation of Eptazocine-Containing Organogel
(1) Isopropyl Myristate (IPM) Organogel
The organogel prepared in the above 1.(2) in Example 2 was used as an IPM organogel.
(2) Isopropyl Palmitate (IPP) Organogel
First, 80.19 mg of EPZ, 199.9 mg of GEFA-$C_8$ and 1729.1 mg of IPP were taken and then mixed while grinding EPZ in a mortar to give an EPZ suspension. Into a test tube were added 1501.2 mg of this suspension [content: EPZ 59.92 mg (2%), GEFA-$C_8$ 149.4 mg (5%)] and 120.9 mg of GP-1 (4%) and further added IPP to give a total amount of 3002.4 mg. Thereafter, an IPP organogel was prepared in the same manner as in the above 1.(2) in Example 2.
(3) 2-Ethylhexyl Palmitate (EHP) Organogel
An EHP organogel was prepared in the same manner as in the above (2) except for using EHP in place of IPP.
(4) Ethyl Stearate (ETS) Organogel
An ETS organogel was prepared in the same manner as in the above (2) except for using ETS in place of IPP.
(5) Ethyl Oleate (ETO) Organogel
An ETO organogel was prepared in the same manner as in the above (2) except for using ETO in place of IPP.
(6) Isopropyl Linoleate (IPLi) Organogel
An IPLi organogel was prepared in the same manner as in the above (2) except for using IPLi in place of IPP.
(7) Diisopropyl Adipate (DIAd) Organogel
A DIAd organogel was prepared in the same manner as in the above (2) except for using DIAd in place of IPP.
(8) Diethyl Sebacate (DESe) Organogel
A DESe organogel was prepared in the same manner as in the above (2) except for using DESe in place of IPP.
2. Mouse Skin Permeation Studies
The mouse skin permeation studies for the EPZ-containing organogels (1) to (8) of various fatty acid esters prepared in the above 1. were carried out in the same manner as in the above Example 3(1), and the amount of EPZ that permeated the skin (n=4) was measured. The permeation rate and the lag time were calculated from each amount of EPZ that permeated the skin. They are shown in Table 6 together with the cumulative amount permeated (after 48 hours). In addition, a graph of the cumulative amount permeated over time is shown in FIG. 9.

TABLE 6

| Example 4 No. | Fatty acid ester | Permeation rate (μg/cm²/hr) | Lag time (hr) | Cumulative amount permeated (after 48 hours) (μg/cm²) |
|---|---|---|---|---|
| (1) | Isopropyl myristate (IPM) | 199.6 ± 10.6 | 1.0 ± 0.1 | 3109.9 ± 80.4 |
| (2) | Isopropyl palmitate (IPP) | 171.7 ± 1.2 | 0.1 ± 0.1 | 3193.0 ± 44.7 |
| (3) | 2-Ethylhexyl palmitate (EHP) | 156.9 ± 14.0 | 0.6 ± 0.1 | 2305.6 ± 93.0 |
| (4) | Ethyl stearate (ETS) | 142.7 ± 19.3 | 0.9 ± 0.3 | 2895.0 ± 123.8 |
| (5) | Ethyl oleate (ETO) | 228.2 ± 13.1 | 0.4 ± 0.3 | 3119.9 ± 283.3 |
| (6) | Isopropyl linoleate (IPLi) | 218.8 ± 3.7 | 0.8 ± 0.1 | 3146.8 ± 35.0 |
| (7) | Diisopropyl adipate (DIAd) | 91.7 ± 16.0 | 6.7 ± 1.3 | 3539.1 ± 302.4 |
| (8) | Diethyl sebacate (DESe) | 131.7 ± 7.4 | 7.6 ± 1.5 | 4139.4 ± 198.3 |

Example 5

Skin Permeability of Organogels to which Various Glycerin Fatty Acid Esters are Added 1. Preparation of Eptazocine-Containing Organogel
(1) 5% Glyceryl Monocaprylate (GEFA-$C_8$)-Added Organogel
The organogel prepared in the above 1.(2) in Example 2 was used as a 5% GEFA-$C_8$-added organogel.
(2) 5% Glyceryl Monocaprate (GEFA-$C_{10}$)-Added Organogel A 5% GEFA-$C_{10}$-added organogel was prepared in the same manner as in the above (1) except for using GEFA-$C_{10}$ in place of GEFA-$C_8$.

(3) 5% Glyceryl Monolaurate (GEFA-$C_{12}$)-Added Organogel

A 5% GEFA-$C_{12}$-added organogel was prepared in the same manner as in the above (1) except for using GEFA-$C_{12}$ in place of GEFA-$C_8$.

(4) 5% Glyceryl Monooleate (GEFA-$C_{18:1}$)-Added Organogel

A 5% GEFA-$C_{18:1}$-added organogel was prepared in the same manner as in the above (1) except for using GEFA-$C_{18:1}$ in place of GEFA-$C_8$.

(5) 5% Glyceryl Dicaprylate (GEFA-di$C_8$)-Added Organogel

A 5% GEFA-di$C_8$-added organogel was prepared in the same manner as in the above (1) except for using GEFA-di$C_5$ in place of GEFA-$C_8$.

(6) 5% Glyceryl Tricaprylate (GEFA-tri$C_8$)-Added Organogel

A 5% GEFA-tri$C_8$-added organogel was prepared in the same manner as in the above (1) except for using GEFA-tri$C_8$ in place of GEFA-$C_8$.

(7) Glycerin Fatty Acid Ester-Free Organogel

First, 80.25 mg of EPZ and 1919.0 mg of IPM were taken and then mixed while grinding EPZ in a mortar to give an EPZ suspension. Into a test tube were added 1614.4 mg of this suspension [content: EPZ 64.80 mg (2%)] and 120.0 mg of GP-1 (4%) and further added IPM to give a total amount of 3017.5 mg. Thereafter, a glycerin fatty acid ester-free organogel was prepared in the same manner as in the above 1.(2) in Example 2.

(8) 2.5% Glyceryl Monocaprylate (GEFA-$C_8$)-Added Organogel

First, 80.59 mg of EPZ, 101.5 mg of GEFA-$C_8$ and 1825.1 mg of IPM were taken and then mixed while grinding EPZ in a mortar to give an EPZ suspension. Into a test tube were added 1502.4 mg of this suspension [content: EPZ 60.32 mg (2%), GEFA-$C_8$ 75.97 mg (2.5%)] and 121.4 mg of GP-1 (4%) and further added IPM to give a total amount of 3003.2 mg. Thereafter, a 2.5% GEFA-$C_8$-added organogel was prepared in the same manner as in the above 1.(2) in Example 2.

(9) 7.5% Glyceryl Monocaprylate (GEFA-$C_8$)-Added Organogel

A 7.5% GEFA-$C_8$-added organogel was prepared in the same manner as in the above (8) such that the final concentration of GEFA-$C_8$ became 7.5%.

(10) 10% Glyceryl Monocaprylate (GEFA-$C_8$)-Added Organogel

A 10% GEFA-$C_8$-added organogel was prepared in the same manner as in the above (8) such that the final concentration of GEFA-$C_8$ became 10%.

2. Mouse Skin Permeation Studies

The mouse skin permeation studies for the EPZ-containing organogels (1) to (10) of various glycerin fatty acid esters prepared in the above 1. were carried out in the same manner as in the above Example 3(1), and the amount of EPZ that permeated the skin (n=4) was measured. The permeation rate and the lag time were calculated from each amount of EPZ that permeated the skin. They are shown in Table 7 together with the cumulative amount permeated (after 48 hours).

TABLE 7

| Example 5 No. | Glycerin fatty acid ester | Permeation rate ($\mu g/cm^2/hr$) | Lag time (hr) | Cumulative amount permeated (after 48 hours) ($\mu g/cm^2$) |
|---|---|---|---|---|
| (1) | 5% Glyceryl monocaprylate (GEFA-$C_8$) | 199.6 ± 10.6 | 1.0 ± 0.1 | 3109.9 ± 80.4 |
| (2) | 5% Glyceryl monocaprate (GEFA-$C_{10}$) | 161.9 ± 26.1 | 1.1 ± 0.1 | 3023.2 ± 186.8 |
| (3) | 5% Glyceryl monolaurate (GEFA-$C_{12}$) | 117.8 ± 17.1 | 2.0 ± 0.1 | 2647.7 ± 95.0 |
| (4) | 5% Glyceryl monooleate (GEFA-$C_{18:1}$) | 52.7 ± 3.0 | 3.2 ± 1.0 | 2240.8 ± 98.1 |
| (5) | 5% Glyceryl dicaprylate (GEFA-di$C_8$) | 48.6 ± 6.1 | 1.8 ± 0.3 | 2142.2 ± 42.1 |
| (6) | 5% Glyceryl tricaprylate (GEFA-tri$C_8$) | 58.8 ± 3.1 | 0.8 ± 0.6 | 2316.1 ± 130.6 |
| (7) | Glycerin fatty acid ester-free | 37.6 ± 5.0 | 5.8 ± 0.8 | 1786.6 ± 169.2 |
| (8) | 2.5% Glyceryl monocaprylate (GEFA-$C_8$) | 153.1 ± 19.7 | 0.7 ± 0.1 | 2947.9 ± 168.6 |
| (9) | 7.5% Glyceryl monocaprylate (GEFA-$C_8$) | 231.8 ± 24.9 | 0.4 ± 0.1 | 3672.0 ± 248.9 |
| (10) | 10% Glyceryl monocaprylate (GEFA-$C_8$) | 213.9 ± 17.5 | 0.2 ± 0.2 | 3400.4 ± 220.5 |

Example 6

Skin Permeability of Organogels in which Drugs at Various Concentrations are Contained 1. Preparation of Eptazocine-Containing Organogel (1) 0.5% Eptazocine-Containing GP-1 Organogel First, 40.17 mg of EPZ, 400.3 mg of GEFA-$C_8$ and 3559.6 mg of IPM were taken and then mixed while grinding EPZ in a mortar to give an EPZ suspension. Into a test tube were added 1518.8 mg of this suspension [content: EPZ 15.25 mg (0.5%), GEFA-$C_8$ 152.0 mg (5%)] and 120.5 mg of GP-1 (4%) and further added IPM to give a total amount of 3008.6 mg. Thereafter, a 0.5% EPZ-containing GP-1 organogel was prepared in the same manner as in the above 1.(2) in Example 2.

(2) 1% Eptazocine-Containing GP-1 Organogel

A 1% EPZ-containing GP-1 organogel was prepared in the same manner as in the above (1) such that the final concentration of EPZ became 1%.

(3) 2% Eptazocine-Containing GP-1 Organogel

The organogel prepared in the above 1.(2) in Example 2 was used as a 2% EPZ-containing GP-1 organogel.

(4) 5% Eptazocine-Containing GP-1 Organogel

A 5% EPZ-containing GP-1 organogel was prepared in the same manner as in the above (1) such that the final concentration of EPZ became 5%.

(5) 10% Eptazocine-Containing GP-1 Organogel

A 10% EPZ-containing GP-1 organogel was prepared in the same manner as in the above (1) such that the final concentration of EPZ became 10%.

(6) 15% Eptazocine-Containing GP-1 Organogel

A 15% EPZ-containing GP-1 organogel was prepared in the same manner as in the above (1) such that the final concentration of EPZ became 15%.

2. Preparation of Tramadol-Containing Organogel (1) 2% Tramadol-Containing EB-21 Organogel Into a test tube were added 60.25 mg of TRD (2%), 153.5 mg of GEFA-$C_8$ (5%) and 119.1 mg of EB-21 (4%) and further added IPM to give a total amount of 3002.0 mg. The test tube was placed in a heating block which had been heated at 145° C., and the mixture solution was heated and stirred to dissolve uniformly. After the mixture solution was dissolved uniformly, the heating block was set to a temperature of 100° C., and the solution was stirred occasionally. When the solution was cooled to 120° C. or less, it was taken out of the heating block and stirred slowly at room temperature until it started to turn into a gel. The stirring was stopped when the solution started to turn into a gel, and this was allowed to stand, so that a 2% TRD-containing EB-21 organogel was obtained.

(2) 10% Tramadol-Containing EB-21 Organogel

Into a test tube were added 300.21 mg of TRD (10%), 150.2 mg of GEFA-$C_8$ (5%) and 120.8 mg of EB-21 (4%) and further added IPM to give a total amount of 3001.7 mg. Thereafter, a 10% TRD-containing EB-21 organogel was prepared in the same manner as in the above (1).

3. Mouse Skin Permeability Testpermeation Studies

The mouse skin permeability testpermeation studies werewas carried out in the same manner as in the above Example 3(1) for the EPZ-containing organogels prepared in the above 1. and in the same manner as in the above Example 3(2) for the TRD-containing organogels prepared in the above 2. respectively, and the amount of drug that permeated the skin (n=4) was measured. The permeation rate and the lag time were calculated from each amount of drug that permeated the skin. They are shown in Table 8 together with the cumulative permeation amount permeated (after 48 hours).

Example 7

Skin Permeability of Organogels in which Gelling Agents at Various Concentrations are Used 1. Preparation of Eptazocine-Containing Organogel (1) 2% GP-1 Organogel First, 200.78 mg of EPZ, 500.4 mg of GEFA-$C_8$ and 4302.9 mg of IPM were taken and then mixed while grinding EPZ in a mortar to give an EPZ suspension. Into a test tube were added 1504.7 mg of this suspension [content: EPZ 60.37 mg (2%), GEFA-$C_8$ 150.5 mg (5%)] and 60.8 mg of GP-1 (2%) and further added IPM to give a total amount of 3001.0 mg. Thereafter, a 2% GP-1 organogel was prepared in the same manner as in the above 1.(2) in Example 2.

(2) 4% GP-1 Organogel

The organogel prepared in the above 1.(2) in Example 2 was used as a 4% GP-1 organogel.

(3) 6% GP-1 Organogel

A 6% GP-1 organogel was prepared in the same manner as in the above (1) such that the final concentration of GP-1 became 6%.

(4) 10% GP-1 Organogel

A 10% GP-1 organogel was prepared in the same manner as in the above (1) such that the final concentration of GP-1 became 10%.

2. Mouse Skin Permeability Testpermeation Studies

The mouse skin permeability testpermeation studies for the organogels of GP-1 at various concentrations (1) to (4) prepared in the above 1. werewas carried out in the same manner as in the above Example 3(1), and the amount of EPZ that permeated the skin (n=4) was measured. The permeation rate and the lag time were calculated from each amount of EPZ that permeated the skin. They are shown in Table 9 together with the cumulative permeation amount permeated (after 48 hours).

TABLE 9

| Example 7 No. | Concentration of GP-1 | Permeation rate ($\mu g/cm^2/hr$) | Lag time (hr) | Cumulative amount permeated (after 48 hours) ($\mu g/cm^2$) |
|---|---|---|---|---|
| (1) | 2% | 223.9 ± 15.3 | 0.1 ± 0.2 | 3536.8 ± 138.9 |
| (2) | 4% | 199.6 ± 10.6 | 1.0 ± 0.1 | 3109.9 ± 80.4 |
| (3) | 6% | 223.8 ± 11.9 | 0.0 ± 0.3 | 3252.2 ± 265.9 |
| (4) | 10% | 203.4 ± 0.2 | 0.2 ± 0.2 | 3151.0 ± 119.1 |

TABLE 8

| Example 6 No. | | Drug | Concentration of drug | Permeation rate ($\mu g/cm^2/hr$) | Lag time (hr) | Cumulative amount permeated (after 48 hours) ($\mu g/cm^2$) |
|---|---|---|---|---|---|---|
| 1 | (1) | EPZ | 0.5% | 60.5 ± 6.1 | 0.6 ± 0.1 | 939.0 ± 110.5 |
|   | (2) |     | 1% | 170.4 ± 6.3 | 0.4 ± 0.1 | 1793.1 ± 53.8 |
|   | (3) |     | 2% | 199.6 ± 10.6 | 1.0 ± 0.1 | 3109.9 ± 80.4 |
|   | (4) |     | 5% | 276.3 ± 26.7 | 0.8 ± 0.1 | 4703.8 ± 409.9 |
|   | (5) |     | 10% | 420.1 ± 33.6 | 0.6 ± 0.2 | 7010.9 ± 377.8 |
|   | (6) |     | 15% | 626.6 ± 85.4 | 0.7 ± 0.2 | 10410.1 ± 505.4 |
| 2 | (1) | TRD | 2% | 761.0 ± 8.5 | 0.3 ± 0.1 | 4172.5 ± 191.8 |
|   | (2) |     | 10% | 3832.1 ± 81.6 | 0.6 ± 0.1 | 21468.5 ± 1071.9 |

Example 8

Skin Permeability of Organogel Prepared by Adding Lower Alcohol

1. Preparation of Eptazocine-Containing Organogel
(1) GP-1 Organogel Prepared by Adding 20% Ethanol First, 159.15 mg of EPZ, 400.5 mg of GEFA-$C_8$ and 3446.2 mg of IPM were taken and then mixed while grinding EPZ in a mortar to give an EPZ suspension. Into a test tube were added 1519.1 mg of this suspension [content: EPZ 60.35 mg (2%), GEFA-$C_8$ 151.9 mg (5%)] and 120.2 mg of GP-1 (4%) and further added IPM to give a total amount of 3092.2 mg. Next, 760 μL of 99.5% ethanol (20%) was added thereto. The test tube was then placed in a heating block which had been heated at 100° C. to heat the mixture solution. The test tube was occasionally taken out of the heating block and stirred to dissolve uniformly. The heating was continued to partially remove ethanol by distillation. The solution was taken out of the heating block and stirred slowly until it started to turn into a gel. The stirring was stopped when the solution started to turn into a gel, and this was dried overnight at 40° C., so that a GP-1 organogel prepared by adding 20% ethanol was obtained.

(2) GP-1 Organogel Prepared by Adding 50% Ethanol

A GP-1 organogel prepared by adding 50% ethanol was obtained in the same manner as in the above (1) except for adding 50% ethanol in the mixture solution.

(3) GELALLOL D Organogel Prepared by Adding 30% Ethanol

First, 79.95 mg of EPZ, 600.6 mg of GEFA-$C_8$ and 1719.1 mg of IPM were taken and then mixed while grinding EPZ in a mortar to give an EPZ suspension. Into a test tube were added 1505.9 mg of this suspension [content: EPZ 60.21 mg (2%), GEFA-$C_8$ 151.1 mg (5%)] and 9.08 mg of GEL ALLOL D (0.3%) and further added IPM to give a total amount of 3007.6 mg. Next, 1200 μL of 99.5% ethanol (30%) was added thereto. The test tube was then placed in a heating block which had been heated at 100° C. to heat the mixture solution. Thereafter, a GEL ALLOL D organogel prepared by adding 30% ethanol was obtained in the same manner as in the above (1).

2. Mouse Skin Permeability Testpermeation Studies

The mouse skin permeability testpermeation studies for the EPZ-containing organogels (1) to (3) prepared by adding ethanol in the above 1. werewas carried out in the same manner as in the above Example 3(1), and the amount of EPZ that permeated the skin (n=4) was measured. The permeation rate and the lag time were calculated from each amount of EPZ that permeated the skin. They are shown in Table 10 together with the cumulative permeation amount permeated (after 48 hours).

TABLE 10

| Example 8 No. | Gelling agent | Concentration of ethanol | Permeation rate (μg/cm$^2$/hr) | Lag time (hr) | Cumulative amount permeated (after 48 hours) (μg/cm$^2$) |
| --- | --- | --- | --- | --- | --- |
| (1) | GP-1 | 20% | 191.3 ± 18.4 | 0.5 ± 0.1 | 2813.5 ± 210.4 |
| (2) | GP-1 | 50% | 204.3 ± 11.4 | 0.6 ± 0.1 | 3089.5 ± 135.0 |
| (3) | GELALL D | 30% | 199.6 ± 7.6 | −0.5 ± 0.4 | 3523.4 ± 123.6 |
| Example 21. (2) | GP-1 | 0% | 199.6 ± 10.6 | 1.0 ± 0.1 | 3109.9 ± 80.4 |

Example 9

Skin Permeability of Organogel Through Drug Release Membrane or Membrane Filter 1. Preparation of Eptazocine-Containing Organogel An EPZ-containing GP-1 organogel prepared in the same manner as in the above 1.(2) in Example 2 was used.

2. Mouse Skin Permeability Testpermeation Studies

The amount of EPZ that permeated the skin (n=4) of the EPZ-containing GP-1 organogel prepared in the above 1. was measured in the same manner as in the above Example 3(1), except that the organogel was applied after each of a drug release membrane (porous polypropylene membrane 4×4 cm, product name: CELGARD 2400, manufactured by POLYPORE International Inc.) or three kinds of membrane filters: membrane filter A [nitrocellulose, 0.20 μm, 133 μm], membrane filter B [tetrafluoroethylene resin, 0.20 μm, 80 μm] and membrane filter C [hydrophilic-treated tetrafluoroethylene resin, 0.20 μm, 35 μm] (material, pore-diameter and thickness are shown in each bracket, and all of which are manufactured by ADVANTEC) was placed on the excised skin of a hairless mouse (donor phase). The permeation rate and the lag time were calculated from each amount of EPZ that permeated the skin. They are shown in Table 11 together with the cumulative permeation amount permeated (after 48 hours).

TABLE 11

| Applied membrane | Permeation rate (μg/cm$^2$/hr) | Lag time (hr) | Cumulative amount permeated (after 48 hours) (μg/cm$^2$) |
| --- | --- | --- | --- |
| Celgard 2400 | 83.6 ± 38.5 | 0.7 ± 0.1 | 1947.4 ± 630.0 |
| Membrane filter A | 92.0 ± 11.6 | 0.8 ± 0.3 | 2428.1 ± 153.9 |
| Membrane filter B | 143.8 ± 12.3 | 0.6 ± 0.2 | 2652.5 ± 240.5 |
| Membrane filter C | 172.4 ± 13.6 | 0.7 ± 0.1 | 2759.3 ± 215.5 |
| Membrane-free | 199.6 ± 10.6 | 1.0 ± 0.1 | 3109.9 ± 80.4 |

Example 10

Skin Permeability of Matrix-Type Patch Preparation in which Organogel is Used 1. Preparation of Adhesive As for an EUDRAGIT E adhesive (acrylic adhesive, manufactured by Evonik Degussa Japan Co., Ltd.) among adhesives used in this example, an adhesive prepared as described below was used. First, 19.9 g, 11.1 g and 2.2 g of acetone, ethanol and 2-propanol, respectively, were weighed into a beaker and stirred to mix uniformly. Then, 37.5 g of aminoalkyl methacrylate copolymer E (EUDRAGIT E PO, manufactured by Evonik Degussa Japan Co., Ltd.) was added thereto gradually while stirring to dissolve. Thereafter, 19.9 g of dibutyl sebacate, which is a plasticizer, was added promptly and stirred for 10 minutes. Lastly, 3.4 g of succinic acid, which is a cross-linking agent, was added gradually while stirring to dissolve solid components completely, so that an EUDRAGIT E adhesive (solid component content 64.7%) was obtained.

As for the other adhesives: DURO-TAK 87-9301 (acrylic adhesive, manufactured by Henkel AG & Co.), BIO-PSA 7-4202 (silicone adhesive, manufactured by Dow Corning Toray Co., Ltd.), QUINTONE M100 (aliphatic hydrocarbon resin adhesive, manufactured by ZEON CORPORATION), QUINTAC 3421 (styrene isoprene block copolymer, manufactured by ZEON CORPORATION), CLEARON P125 (hydrogenated terpene resin adhesive, manufactured by YASUHARA CHEMICAL CO., LTD.) and ESTER GUM H (hydrogenated rosin ester resin, Arakawa Chemical Industries, Ltd.), these were each dissolved in a solvent appropriately and used with the use of a plasticizer and a cross-linking agent as needed.

2. Preparation of Eptazocine-Containing Organogel Matrix-Type Patch Preparation

A. GP-1 Organogel Matrix-Type Patch Preparation (Adhesive, Coating Thickness)

(1) 2% Eptazocine-Containing Patch Preparation (EUDRAGIT E 50%, 250 μm)

First, 20.27 mg (2%) of EPZ, 52.1 mg (5%) of GEFA-$C_8$, 39.6 mg (4%) of GP-1 and 388.4 mg (39%) of IPM were weighed respectively and added to a test tube. Next, 785.7 mg of the EUDRAGIT E adhesive (solid component 500.5 mg) was added thereto to give a total amount (solid component 1000.87 mg), and then 500 μL of ethanol was added thereto. The test tube was placed in a heating block which had been heated at 90° C., and the mixture solution was heated and stirred to dissolve uniformly. This solution was coated onto a support (product name: SCOTCHPAK 9732 Backing, manufactured by 3M Company) which had been fixed on a flat glass plate, at a thickness of 250 μm with the use of a film applicator (product name: MULTICATOR 411, manufactured by ERICHSEN Gmbh & Co. KG). Then, the coated support was dried at 60° C. for 30 minutes in a constant temperature fan dryingforced air flow oven. After drying, the fluororesin-coated surface of a detachable film (product name: SCOTCHPAK 1022 Release Liner, manufactured by 3M Company) was bonded to the adhesiveon surface of the preparation, to give a 2% EPZ-containing patch preparation (EUDRAGIT E 50%).

(2) 2% Eptazocine-Containing Patch Preparation (DURO-TAK 87-9301 50%, 250 μm)

First, 20.72 mg (2%) of EPZ, 50.3 mg (5%) of GEFA-$C_8$, 41.3 mg (4%) of GP-1 and 396.8 mg (39%) of IPM were weighed respectively and added to a test tube. Next, 1239.9 mg of the DURO-TAK 87-9301 adhesive (solid component 496.0 mg) was added thereto to give a total amount (solid component 1005.1 mg), and then 700 μL of ethanol was added thereto. Thereafter, a 2% EPZ-containing patch preparation (DURO-TAK 87-9301 50%) was prepared in the same manner as in the above (1).

(3) 2% Eptazocine-Containing Patch Preparation (BIO-PSA 7-4202 50%, 250 μm)

First, 20.17 mg (2%) of EPZ, 49.9 mg (5%) of GEFA-$C_8$, 41.0 mg (4%) of GP-1 and 390.4 mg (39%) of IPM were weighed respectively and added to a test tube. Next, 837.6 mg of the BIO-PSA 7-4202 adhesive (solid component 502.6 mg) was added thereto to give a total amount (solid component 1004.1 mg), and then 700 μL of ethanol was added thereto. Thereafter, a 2% EPZ-containing patch preparation (BIO-PSA 7-4202 50%) was prepared in the same manner as in the above (1).

(4) 2% Eptazocine-Containing Patch Preparation (EUDRAGIT E 50%, 400 μm)

First, 20.32 mg (2%) of EPZ, 50.4 mg (5%) of GEFA-$C_8$, 40.8 mg (4%) of GP-1 and 393.1 mg (39%) of IPM were weighed respectively and added to a test tube. Next, 787.8 mg of the EUDRAGIT E adhesive (solid component 501.8 mg) was added thereto to give a total amount (solid component 1006.4 mg), and then 500 μL of ethanol was added thereto. Thereafter, a 2% EPZ-containing patch preparation (EUDRAGIT E 50%) was prepared in the same manner as in the above (1), except for changing the coating thickness to 400 μm.

(5) 5% Eptazocine-Containing Patch Preparation (EUDRAGIT E 50%, 400 μm)

First, 50.20 mg (5%) of EPZ, 51.5 mg (5%) of GEFA-$C_8$, 40.1 mg (4%) of GP-1 and 376.8 mg (36%) of IPM were weighed respectively and added to a test tube. Next, 789.2 mg of the EUDRAGIT E adhesive (solid component 502.7 mg) was added thereto to give a total amount (solid component 1021.3 mg), and then 1500 μL of ethanol was added thereto. Thereafter, a 5% EPZ-containing patch preparation (EUDRAGIT E 50%) was prepared in the same manner as in the above (4).

B. EB-21 Organogel Matrix-Type Patch Preparation (1) 2% Eptazocine-Containing Patch Preparation (EUDRAGIT E 50%, 400 μm)

First, 20.27 mg (2%) of EPZ, 52.1 mg (5%) of GEFA-$C_8$, 39.6 mg (4%) of EB-21 and 388.4 mg (39%) of IPM were weighed respectively and added to a test tube. Next, 785.7 mg of the EUDRAGIT E adhesive (solid component 500.5 mg) was added thereto to give a total amount (solid component 1000.87 mg), and then 500 μL of ethanol was added thereto. Thereafter, a 2% EPZ-containing patch preparation (EUDRAGIT E 50%) was prepared in the same manner as in the above A.(4).

(2) 5% Eptazocine-Containing Patch Preparation (EUDRAGIT E 50%, 400 μm)

First, 50.68 mg (5%) of EPZ, 49.6 mg (5%) of GEFA-$C_8$, 40.5 mg (4%) of EB-21 and 360.0 mg (36%) of IPM were weighed respectively and added to a test tube. Next, 786.4 mg of the EUDRAGIT E adhesive (solid component 500.9 mg) was added thereto to give a total amount (solid component 1001.7 mg), and then 1000 μL of ethanol was added thereto. Thereafter, a 5% EPZ-containing patch preparation (EUDRAGIT E 50%) was prepared in the same manner as in the above A.(4).

(3) 10% Eptazocine-Containing Patch Preparation (EUDRAGIT E 50%, 400 μm)

First, 99.90 mg (10%) of EPZ, 50.6 mg (5%) of GEFA-$C_8$, 40.7 mg (4%) of EB-21 and 310.6 mg (31%) of IPM were weighed respectively and added to a test tube. Next, 790.1 mg of the EUDRAGIT E adhesive (solid component 503.3 mg) was added thereto to give a total amount (solid component 1005.1 mg), and then 2500 μL of ethanol was added thereto. Thereafter, a 10% EPZ-containing patch preparation (EUDRAGIT E adhesive 50%) was prepared in the same manner as in the above A.(4).

(4) 15% Eptazocine-Containing Patch Preparation (EUDRAGIT E 40%, 400 μm)

First, 151.66 mg (15%) of EPZ, 49.6 mg (5%) of GEFA-$C_8$, 40.8 mg (4%) of EB-21 and 363.8 mg (36%) of IPM were weighed respectively and added to a test tube. Next, 636.3 mg of the EUDRAGIT E adhesive (solid component 405.3 mg) was added thereto to give a total amount (solid component 1011.2 mg), and then 3300 µL of ethanol was added thereto. The test tube was placed in a heating block which had been heated at 90° C., and the mixture solution was heated and stirred to dissolve uniformly. Next, 100 µL of this solution was dispensed into a mold (φ15×1 mm) covered with aluminum foil. Then, this was dried at 60° C. for 3 hours and at 40° C. for 15 hours in a constant temperature fan dryingforced air flow oven. After drying, the fluororesin-coated surface of a detachable film (SCOTCHPAK 1022 Release Liner) was bonded to the adhesiveon surface of the preparation, to give a 15% EPZ-containing patch preparation (EUDRAGIT E 40%).

(5) 2% Eptazocine-Containing Patch Preparation (EUDRAGIT E 50%, 250 µm)

First, 40.72 mg (2%) of EPZ, 101.4 mg (5%) of GEFA-$C_8$, 80.5 mg (4%) of EB-21 and 782.5 mg (39%) of IPM were weighed respectively and added to a test tube. Next, 1566.1 mg of the EUDRAGIT E adhesive (solid component 1003.9 mg) was added thereto to give a total amount (solid component 2008.9 mg), and then 500 µL of ethanol was added thereto. The test tube was placed in a heating block which had been heated at 90° C., and the mixture solution was heated and stirred to dissolve uniformly. This solution was coated onto a support (SCOTCHPAK 9732 Backing) which had been fixed on a flat glass plate, at a thickness of 250 µm with the use of a film applicator (MULTICATOR 411). Then, this was dried at 600° C. for 1.5 hours and at 40° C. for 15 hours in a constant temperature fan dryingforced air flow oven. After drying, the fluororesin-coated surface of a detachable film (SCOTCHPAK 1022 Release Liner) was bonded to the adhesiveon surface of the preparation, to give a 2% EPZ-containing patch preparation (EUDRAGIT E 50%).

(6) 2% Eptazocine-Containing Patch Preparation (EUDRAGIT E 70%, 250 µm)

First, 40.66 mg (2%) of EPZ, 100.9 mg (5%) of GEFA-$C_8$, 80.7 mg (4%) of EB-21 and 382.5 mg (19%) of IPM were weighed respectively and added to a test tube. Next, 2186.0 mg of the EUDRAGIT E adhesive (solid component 1401.3 mg) was added thereto to give a total amount (solid component 2006.0 mg), and then 500 µL of ethanol was added thereto. Thereafter, a 2% EPZ-containing patch preparation (EUDRAGIT E 70%) was prepared in the same manner as in the above (5).

(7) 2% Eptazocine-Containing Patch Preparation (EUDRAGIT E 50%+DURO-TAK 87-9301 10%, 250 µm)

First, 20.77 mg (2%) of EPZ, 49.8 mg (5%) of GEFA-$C_8$, 41.4 mg (4%) of EB-21 and 288.7 mg (29%) of IPM were weighed respectively and added to a test tube. Next, 775.7 mg of the EUDRAGIT E adhesive (solid component 497.2 mg) and 277.7 mg of the DURO-TAK 87-9301 adhesive (solid component content 60%) (solid component 111.1 mg) were added thereto to give a total amount (solid component 1009.0 mg), and then 500 µL of ethanol was added thereto. Thereafter, a 2% EPZ-containing patch preparation (EUDRAGIT E 50%+DURO-TAK 87-9301 10%) was prepared in the same manner as in the above (5).

(8) 2% Eptazocine-Containing Patch Preparation (EUDRAGIT E 50%+QUINTONE M100 10%, 250 µm)

First, 20.48 mg (2%) of EPZ, 53.0 mg (5%) of GEFA-$C_8$, 40.3 mg (4%) of EB-21 and 289.6 mg (29%) of IPM were weighed respectively and added to a test tube. Next, 797.8 mg of the EUDRAGIT E adhesive (solid component 511.4 mg) and 500 µL of ethanol were added thereto. The test tube was placed in a heating block which had been heated at 90° C., and the mixture solution was heated and stirred to dissolve uniformly. Next, 99.4 mg of QUINTONE M100 (10%) was added thereto to give a total amount (solid component 1014.1 mg), and then 1000 µL of ethyl acetate was added thereto. Thereafter, a 2% EPZ-containing patch preparation (EUDRAGIT E 50%+QUINTONE M100 10%) was prepared in the same manner as in the above (5).

(9) 2% Eptazocine-Containing Patch Preparation (QUINTONE M100 27%+QUINTAC 3421 22%, 250 µm)

First, 21.51 mg (2%) of EPZ, 50.7 mg (5%) of GEFA-$C_8$, 41.7 mg (4%) of EB-21 and 401.1 mg (40%) of IPM were weighed respectively and added to a test tube. Next, 500 µL of ethanol was added thereto. The test tube was placed in a heating block which had been heated at 120° C., and the mixture solution was heated and stirred to dissolve uniformly. Then, 269.3 mg of QUINTONE M100 (27%) and 220.6 mg of QUINTAC 3421 (22%) were added thereto to give a total amount (solid component 1004.8 mg), and thereafter 1500 µL of toluene was added thereto. The test tube was placed in a heating block which had been heated at 120° C., and the mixture solution was heated and stirred to dissolve uniformly. Thereafter, a 2% EPZ-containing patch preparation (QUINTONE M100 27%+QUINTAC 3421 22%) was prepared in the same manner as in the above (5).

(10) 2% Eptazocine-Containing Patch Preparation (EUDRAGIT E 35%+QUINTONE M100 6%+QUINTAC 3421 5%, 250 µm)

First, 23.0 mg (2%) of EPZ, 51.5 mg (5%) of GEFA-$C_8$, 40.3 mg (4%) of EB-21 and 430.9 mg (43%) of IPM were weighed respectively and added to a test tube. Next, 552.1 mg of the EUDRAGIT E adhesive (solid component 353.9 mg) and 500 µL of ethanol were added thereto. The test tube was placed in a heating block which had been heated at 120° C., and the mixture solution was heated and stirred to dissolve uniformly. Then, 62.4 mg of QUINTONE M100 (6%) and 53.9 mg of QUINTAC 3421 (5%) were added thereto to give a total amount (solid component 1015.8 mg), and thereafter 1500 µL of toluene was added thereto. Thereafter, a 2% EPZ-containing patch preparation (EUDRAGIT E 35%+QUINTONE M100 6%+QUINTAC 3421 5%) was prepared in the same manner as in the above (9).

(11) 2% Eptazocine-Containing Patch Preparation (EUDRAGIT E 30%+QUINTAC 3421 10%+CLEARON P125 10%, 250 µm)

First, 20.76 mg (2%) of EPZ, 51.7 mg (5%) of GEFA-$C_8$, 39.8 mg (4%) of EB-21 and 389.3 mg.(39%) of IPM were weighed respectively and added to a test tube. Next, 488.1 mg of the EUDRAGIT E adhesive (solid component 309.5 mg) and 200 µL of ethanol were added thereto. The test tube was placed in a heating block which had been heated at 100° C., and the mixture solution was heated and stirred to dissolve uniformly. Then, 104.6 mg of QUINTAC 3421 (10%) and 100.8 mg of CLEARON P125 (10%) were added thereto to give a total amount (solid component 1016.4 mg), and then 1000 µL of toluene was added thereto. Thereafter, a 2% EPZ-containing patch preparation (EUDRAGIT E 30%+QUINTAC 3421 10%+CLEARON P125 10%) was prepared in the same manner as in the above (9).

(12) 2% Eptazocine-Containing Patch Preparation (QUINTAC 3421 27%+ESTER GUM H 27%, 250 µm)

First, 20.05 mg (2%) of EPZ, 51.0 mg (5%) of GEFA-$C_8$, 40.2 mg (4%) of EB-21 and 349.8 mg (35%) of IPM were weighed respectively and added to a test tube. Next, 400 µL of ethanol was added thereto. The test tube was placed in a heating block which had been heated at 120° C., and the mixture solution was heated and stirred to dissolve uniformly. Then, 268.0 mg of QUINTAC 3421 (27%) and 270.5 mg of ESTER GUM H (27%) were added thereto to give a total amount (solid component 999.4 mg), and then 1500 µL of toluene was added thereto. Thereafter, a 2% EPZ-containing patch preparation (QUINTAC 3421 27%+ESTER GUM H 27%) was prepared in the same manner as in the above Example (9).

3. Preparation of Tramadol-Containing Organogel Matrix-Type Patch Preparation

First, 100.38 mg (10%) of TRD, 312.8 mg (31%) of IPM, 51.30 mg (5%) of GEFA-$C_8$ and 43.40 mg (4%) of EB-21 were weighed respectively and added to a test tube. Next, 790.5 mg of the EUDRAGIT E adhesive (solid component 507.3 mg) was added thereto to give a total amount (solid component 1015.2 mg), and then 300 μL of ethanol was added thereto. The test tube was placed in a heating block which had been heated at 100° C., and the mixture solution was heated and stirred to dissolve uniformly. This solution was coated onto a support (SCOTCHPAK 9732 Backing) which had been fixed on a flat glass plate, at a thickness of 250 μm with the use of a film applicator (MULTICATOR 411). Then, this was dried at 60° C. for 1 hour and at 40° C. overnight in a constant temperature fan dryingforced air flow oven. After drying, the fluororesin-coated surface of a detachable film (SCOTCHPAK 1022 Release Liner) was bonded to the adhesiveon surface of the preparation, to give a 10% TRD-containing patch preparation (EUDRAGIT E 50%).

4. Preparation of Pentazocine-Containing Organogel Matrix-Type Patch Preparation First, 101.00 mg (10%) of PTZ, 320.1 mg (31%) of IPM, 61.1 mg (5%) of GEFA-$C_8$ and 40.6 mg (4%) of EB-21 were weighed respectively and added to a test tube. Next, 783.5 mg of the EUDRAGIT E adhesive (solid component 502.2 mg) was added thereto to give a total amount (solid component 1025.0 mg), and then 300 μL of ethanol was added thereto. The test tube was placed in a heating block which had been heated at 90° C., and the mixture solution was heated and stirred to dissolve uniformly. This solution was coated onto a support (SCOTCHPAK 9732 Backing) which had been fixed on a flat glass plate, at a thickness of 250 μm with the use of a film applicator (MULTICATOR 411). Then, this was dried at 60° C. for 1 hour and at 400° C. for 15 hours in a constant temperature fan dryingforced air flow oven. After drying, the fluororesin-coated surface of a detachable film (SCOTCHPAK 1022 Release Liner) was bonded to the adhesiveon surface of the preparation, to give a 10% PTZ-containing patch preparation (EUDRAGIT E 50%).

5. Mouse Skin Permeability Testpermeation Studies

The mouse skin permeability testpermeation studies werewas carried out in the same manner as in the above Example 3(1) for the EPZ-containing patch preparations prepared in the above 1., in the same manner as in the above Example 3(2) for the TRD-containing patch preparation prepared in the above 3. and in the same manner as in the above Example 3(3) for the PTZ-containing patch preparation prepared in the above 4., respectively, except for applying each of the drug-containing patch preparations (φ12 mm) prepared in the above 2. to 4. on the excised skin of a male hairless mouse (donor phase) in place of the organogel, and each amount of drug that permeated the skin (n=4) was measured. The permeation rate and the lag time were calculated from each amount of drug that permeated the skin. They are shown in Tables 12 and 13 together with the cumulative permeation amount permeated (after 28 hours for the above 2.B.(5) to (12) and after 48 hours for the others). In addition, graphs of the cumulative permeation amount permeated over time of the EPZ-containing patch preparations of the above 2.B.(1) to (4), the TRD-containing patch preparation of the above 3. and the PTZ-containing patch preparation of the above 4. are shown in Tables 10 to 12, respectively.

TABLE 12

| Example 10 No. | | Concentration of drug | Adhesive | Permeation rate (μg/cm²/hr) | Lag time (hr) | Cumulative amount permeated (after 48 hours) (μg/cm²) |
|---|---|---|---|---|---|---|
| 2 | | | A. EPZ-containing GP-1 organogel patch preparation | | | |
| | (1) | EPZ 2% | Eudragit E (50%) | 27.0 ± 5.7 | 1.1 ± 0.2 | 253.3 ± 53.7 |
| | (2) | EPZ 2% | Duro-Tak 87-9301 (50%) | 15.1 ± 1.6 | 2.0 ± 0.1 | 190.4 ± 14.0 |
| | (3) | EPZ 2% | BIO-PSA 7-4202 (50%) | 31.8 ± 7.8 | 0.6 ± 0.2 | 173.6 ± 30.9 |
| | (4) | EPZ 2% | Eudragit E (50%) | 30.5 ± 1.5 | 1.2 ± 0.2 | 358.3 ± 13.5 |
| | (5) | EPZ 5% | Eudragit E (50%) | 59.9 ± 12.7 | 1.7 ± 0.3 | 889.6 ± 110.7 |
| | | | B. EPZ-containing EB-21 organogel patch preparation | | | |
| | (1) | EPZ 2% | Eudragit E (50%) | 52.7 ± 1.5 | 1.1 ± 0.1 | 411.9 ± 18.0 |
| | (2) | EPZ 5% | Eudragit E (50%) | 73.8 ± 13.2 | 1.2 ± 0.1 | 963.3 ± 117.6 |
| | (3) | EPZ 10% | Eudragit E (50%) | 109.1 ± 37.3 | 3.2 ± 0.2 | 1365.9 ± 120.6 |
| | (4) | EPZ 15% | Eudragit E (40%) | 90.7 ± 10.9 | 4.4 ± 0.6 | 2577.3 ± 59.2 |
| 3 | | TRD 10% | Eudragit E (50%) | 155.6 ± 8.4 | 0.5 ± 0.1 | 1128.3 ± 21.3 |
| 4 | | PTZ 10% | Eudragit E (50%) | 44.0 ± 5.5 | 1.9 ± 0.3 | 982.5 ± 110.8 |

TABLE 13

| Example 10 No. | | Concentration of drug | Adhesive | Permeation rate (μg/cm²/hr) | Lag time (hr) | Cumulative amount permeated (after 28 hours) (μg/cm²) |
|---|---|---|---|---|---|---|
| 2 | | | B. EPZ-containing EB-21 organogel patch preparation | | | |
| | (5) | EPZ 2% | Eudragit E (50%) | 33.4 ± 3.9 | 1.2 ± 0.03 | 252.6 ± 11.5 |
| | (6) | EPZ 2% | Eudragit E (70%) | 21.3 ± 3.0 | 1.7 ± 0.1 | 255.6 ± 19.2 |
| | (7) | EPZ 2% | Eudragit E (50%) Duro-Tak 87-9301 (10%) | 18.7 ± 2.8 | 1.8 ± 0.2 | 242.8 ± 12.9 |

TABLE 13-continued

| Example 10 No. | Concentration of drug | Adhesive | Permeation rate (μg/cm²/hr) | Lag time (hr) | Cumulative amount permeated (after 28 hours) (μg/cm²) |
|---|---|---|---|---|---|
| (8) | EPZ 2% | Eudragit E (50%) Quintone M100 (10%) | 22.6 ± 3.9 | 1.5 ± 0.2 | 200.9 ± 6.0 |
| (9) | EPZ 2% | Quintone M100 (27%) Quintac 3421 (22%) | 15.9 ± 0.5 | 0.9 ± 0.3 | 145.0 ± 7.0 |
| (10) | EPZ 2% | Eudragit E (35%) Quintone M100 (6%) Quintac 3421 (5%) | 35.5 ± 3.4 | 0.5 ± 0.1 | 155.4 ± 13.7 |
| (11) | EPZ 2% | Eudragit E (30%) Clearon P125 (10%) Quintac 3421 (10%) | 14.6 ± 1.6 | 1.1 ± 0.2 | 109.5 ± 10.7 |
| (12) | EPZ 2% | Ester Gum H (27%) Quintac 3421 (27%) | 22.2 ± 2.1 | 0.5 ± 0.2 | 128.3 ± 4.5 |

Result

As demonstrated in Reference 1, the matrix-type patch preparations with various acrylic adhesives, the formulation of which is shown in Table 1, did not provide good skin permeability of EPZ as shown in FIG. 1 and Table 2. That is, although they were drug-containing matrices, each having a high drug concentration of 10% or 20%, the permeation rate and the cumulative permeation amount permeated thereof were much lower than those of the 2% EPZ-containing organogels (Tables 2 and 5).

In contrast, it was found that, when EPZ in free form was prepared into an organogel containing a fatty acid ester and a glycerolglycerin fatty acid ester, the resulting organogel showed excellent skin permeability in terms of the skin permeation rate and the drug release rate from the preparation in the skin permeability testpermeation studies with the use of the excised skin of a hairless mouse (Tables 3 and 4).

Also, according to the results of the skin permeability testpermeation studies of the EPZ-containing organogel (1. (2) in Example 2) with the use of the epidermis (shoulder) of a swine (Yucatan miniature swine) whose skin form and drug permeability are regarded to be closer to a human when compared with a hairless mouse, it was observed that the cumulative permeation amount permeated after 48 hours was 62% based on the case of the skin of a hairless mouse, showing that EPZ surely permeated the skin of a swine.

In the case of the suspensions, as shown in FIG. 2, both of the suspension EPZ in free form (0.6% EPZ) and the suspension EPZ in hydrobromide form (0.6% as EPZ) permeated the skin very quickly, and almost all of the drug was released completely after 4 hours. In contrast, in the case of the EPZ-containing organogel, the drug was released in a sustained manner. Therefore, the EPZ-containing organogel can control the drug delivery to the body appropriately by adjusting the concentration of the drug. In some cases, transdermal administration preparations are desired to have characteristics that can deliver drugs at a controlled rate for a long term compared with injectable preparations and oral administration preparations, and the pharmaceutical composition for external use according to the present invention matches such an object. It is to be noted that, in the case of EPZ.HBr and TRD.HCl, even though they were prepared into organogels, the resulting organogels had very low skin permeability, and simply changing a liquid form to an organogel did not necessarily provide excellent skin permeability.

In addition, a comparison was made between the drug release rate from the preparation after 48 hours of the EPZ-containing organogel and that of the EPZ-containing suspension, and the suspension released about 92% of EPZ applied, while the organogel preparation (use of GP-1) released about 96% of EPZ. In general, preparations in matrix or gel form are considered to be low in drug release rate due to the restriction of drug release compared with preparations in liquid form having flowability; however, the pharmaceutical composition for external use according to the present invention showed a very high drug release rate that exceeded that of the preparation in liquid form. Accordingly, the preparation produced by using the pharmaceutical composition for external use according to the present invention, which allows the amount of drug remaining after use to be relatively small, is very efficient and economical as a pharmaceutical preparation and beneficial in terms of management of the drug.

As shown in FIGS. 3 to 6 and Table 5, the EPZ-containing organogels produced by using various organogelling agents such as N-acylamino acid amides (GP-1, EB-21) and dextrin fatty acid esters (RHEOPEARL KL2, RHEOPEARL KS2) showed excellent skin permeability (see Example 3). Also, the results of the skin permeability testpermeation studies of the EPZ-containing GP-1 or EB-21 organogels prepared in different methods are shown in FIGS. 3 and 4. The first preparation method of first method is a method of mixing all components and turning them into a gel, and the second preparation method of second method is a method of adding EPZ to an appropriate amount of components other than an organogelling agent (a fatty acid ester, or a fatty acid ester and a glycerolglycerin fatty acid ester), and then mixing them while grinding EPZ, before addition of the organogelling agent. According to the second preparation method of second method, it was clearly shown that drugs in a suspension state in the pharmaceutical composition for external use according to the present invention, such as EPZ, provided further excellent skin permeability.

As for other non-narcotic analgesics, the organogels containing TRD (FIG. 7) or PTZ (FIG. 8) showed the results of excellent transdermal absorption (Table 5), similar to the EPZ-containing organogel (Table 5). As for TRD, the TRD.HCl-containing GP-1 organogel had very low skin permeability, similar to EPZ.HBr, showing that salts with high hydrophilicity were not appropriate (see Example 3).

The above results clearly show that the pharmaceutical composition for external use according to the present invention produced by using a glycerolglycerin fatty acid ester such as GEFA-$C_8$ and a fatty acid ester such as IPM in combination significantly increases the transdermal absorbability of not only EPZ but also various non-narcotic analgesics.

The present invention is a pharmaceutical composition for external use which is an organogel containing a fatty acid ester and a glycerolglycerin fatty acid ester, and it can use various fatty acid esters as shown in Table 6 and FIG. 9. In particular, the EPZ-containing organogel compositions produced by adding isopropyl myristate, isopropyl palmitate, ethyl oleate orand isopropyl linoleate showed excellent skin permeability (see Example 4).

Similarly, the present invention can use various glycerolglycerin fatty acid esters as shown in Table 7. In particular, the EPZ-containing organogel compositions produced by adding glycerolglyceryl monocaprylate, glycerolglyceryl monocaprate orand glycerolglyceryl monolaurate showed excellent skin permeability. In terms of the concentration of the glycerolglycerin fatty acid ester to be added, as shown in the results of glycerolglyceryl monocaprylate in Table 7(1) and (8) to (10), the skin permeability was improved in a concentration dependent manner until the concentration reached 7.5%, and the skin permeability in the case of 10% concentration was similar to that in the case of 7.5% (see Example 5).

In terms of the drug concentration of the pharmaceutical composition for external use according to the present invention, as shown in Table 8, it was observed that the skin permeability was improved as the concentration of EPZ was increased and it was good even at a high drug concentration of 15% (see Example 6). As for TRD, it was shown that the skin permeability was good in a concentration dependent manner at both concentrations of 2% and 10%.

In terms of the concentration of the organogelling agent of the pharmaceutical composition for external use according to the present invention, as shown in Table 9, the GP-1 gelling agent within a concentration range of 2% to 10% did not show particular difference in skin permeability, and the skin permeability was good (see Example 7).

In the present invention, an organogel composition can be prepared by adding a lower alcohol such as ethanol (See Example 8). As shown in Table 10, EPZ skin permeability was good when the lower alcohol was added, in the same manner as in the case where no lower alcohol was added. In this way, the temperature at the time of preparation can be decreased to 100° C. or less by adding a lower alcohol, so that water vapor can be used as a heat medium in the actual production process, which is highly beneficial in practice. In Example 8, organogel compositions were prepared by using GP-1 or GELALLOL D as a gelling agent; however, other gelling agents such as EB-21 can be also used. The addition of a lower alcohol can be also applied in preparing a matrix-type patch preparation in which an adhesive is added to the pharmaceutical composition for external use according to the present invention.

In the skin permeability testpermeation studies of the pharmaceutical composition for external use according to the present invention with the use of a drug release membrane or the like (see Example 9), in which a reservoir-type patch preparation was assumed, the skin permeability was sufficient in terms of availability, although the skin permeation rate of EPZ was decreased compared with the case where no drug release membrane or the like was used, as shown in Table 11. The results show that the pharmaceutical composition for external use according to the present invention can be applied to a reservoir-type patch preparation.

Figure 10:
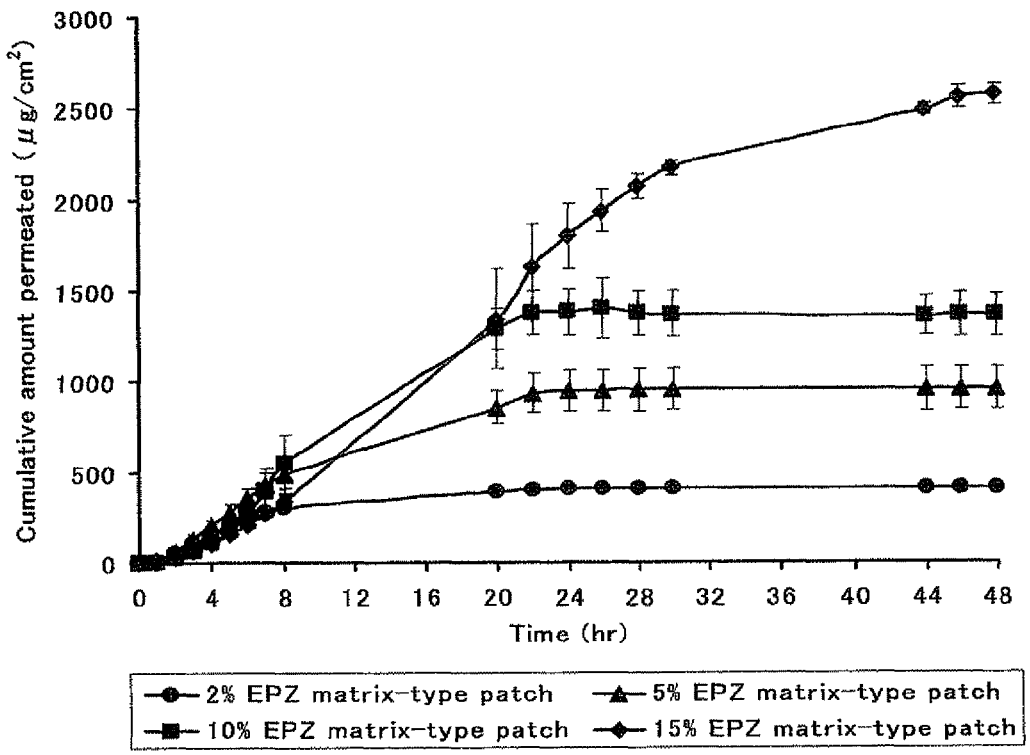
FIG. 10 is a graph showing the cumulative amount of eptazocine permeated through the skin over time in a skin permeation study of matrix-type patch preparations with the use of eptazocine-containing EB-21 organogels.
Figure 11:
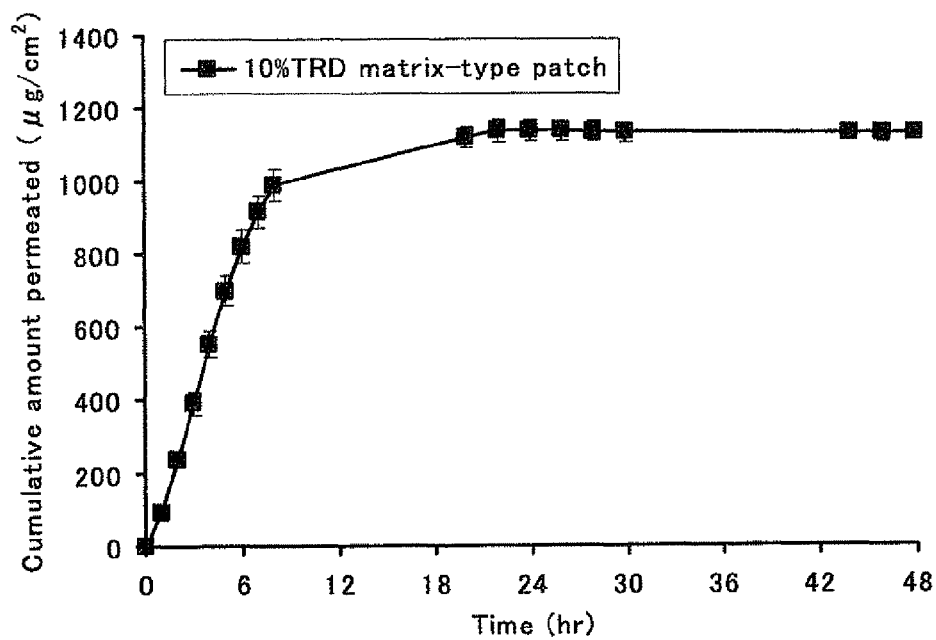
FIG. 11 is a graph showing the cumulative amount of tramadol permeated through the skin over time in a skin permeation study of a matrix-type patch preparation with the use of a tramadol-containing EB-21 organogel.
Figure 12:
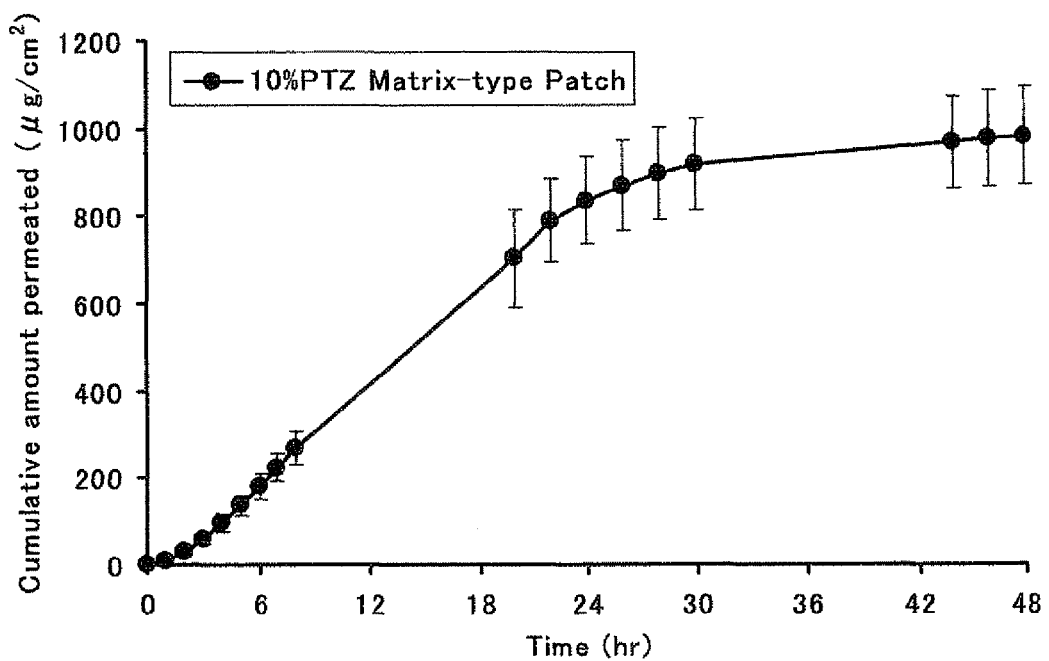
FIG. 12 is a graph showing the cumulative amount of pentazocine permeated through the skin over time in a skin permeation study of a matrix-type patch preparation with the use of a pentazocine-containing EB-21 organogel.

In the skin permeability testpermeation studies of the matrix-type patch preparations with the use of the pharmaceutical composition for external use according to the present invention (see Example 10), as shown in Tables 12 and 13 and FIGS. 10 to 12, the matrix-type patch preparations prepared by using the adhesives were capable of delivering the drug into the body with satisfactory skin permeation rate in a sustained manner. The skin permeability of drugs in the matrix-type patch preparations was observed in the organogel compositions in which various adhesives were used, not only for EPZ but also TRD and PTZ. The results show that the pharmaceutical composition for external use according to the present invention can be applied to matrix-type patch preparations in which various adhesives are used.

INDUSTRIAL APPLICABILITY

The pharmaceutical composition for external use according to the present invention can significantly improve skin permeability of drugs such as non-narcotic analgesics and allows a sufficient amount of drug to permeate the skin sustainably, thereby achieving a high therapeutic effect. Further, the pharmaceutical composition for external use according to the present invention releases drugs gradually, so that it can be easily applied to a preparation capable of controlling the amount of drug delivery. Particularly In addition, the pharmaceutical composition for external use according to the present invention is in organogel form which can be easily put into practical use as actual preparations such as patch and gel preparations and therefore is highly beneficial in practice, and it has a very high drug release rate and therefore can make efficient use and management of the applied drug.

The invention claimed is:
1. A matrix-type patch preparation comprising:
   a support; and
   an adhesive base layer having:
      an adhesive; and
      a pharmaceutical composition for external use, which is an organogel containing:
         0.1 to 20 wt % of an organogelling agent that is dibutyl lauroyl glutamide and/or dibutyl ethylhexanoyl glutamide;
         0.01 to 20 wt % of a non-narcotic analgesic in free form selected from the group consisting of eptazocine, tramadol, and pentazocine;
         30 to 95 wt % of a fatty acid ester selected from the group consisting of isopropyl myristate, isopropyl palmitate, ethyl oleate, and isopropyl linoleate; and
         1 to 20 wt % of a glycerin fatty acid ester having a fatty acid of 8 to 12 carbon atoms,
   based on a total weight of the pharmaceutical composition.
2. The matrix-type patch preparation according to claim 1, wherein the fatty acid ester is isopropyl myristate or isopropyl palmitate.
3. The matrix-type patch preparation according to claim 1, wherein the glycerin fatty acid ester is glyceryl monocaprylate, glyceryl monocaprate, or glyceryl monolaurate.
4. The matrix-type patch preparation according to claim 3, wherein the glycerin fatty acid ester is glyceryl monocaprylate or glyceryl monocaprate.
5. The matrix-type patch preparation according to claim 1, wherein the adhesive comprises one or more selected from the group consisting of acrylic resins, silicone resins, styrene isoprene block copolymers, aliphatic hydrocarbon resins, alicyclic saturated hydrocarbon resins, terpene resins, rosin ester resins, and polyisobutylene resins.
6. The matrix-type patch preparation according to claim 1, which is a sustained-release preparation.
7. The matrix-type patch preparation according to claim 6, which is a sustained-release preparation configured to be applied once per day.
8. The matrix-type patch preparation according to claim 6, which is a sustained-release preparation configured to be applied once per two days.

9. A method for producing the matrix-type patch preparation according to claim 1, comprising the steps of:

produce a pharmaceutical composition for external use by mixing together:

0.1 to 20 wt % of the organogelling agent;

0.01 to 20 wt % of the non-narcotic analgesic;

30 to 95 wt % of the fatty acid ester; and 1 to 20 wt % of the glycerin fatty acid ester;

based on the total weight of the pharmaceutical composition;

adding the adhesive to the pharmaceutical composition for external use to produce the adhesive base; and laminating the adhesive base on the support.

10. The method according to claim 9, wherein the mixing together comprises mixing eptazocine in free form with the fatty acid ester or with the fatty acid ester and the glycerin fatty acid ester while grinding eptazocine, and before addition of the organogelling agent.

11. The method according to claim 9, further comprising adding a lower alcohol to the mixture of the non-narcotic analgesic, the fatty acid ester, the glycerin fatty acid ester, and the organogelling agent.

12. The method according to claim 11, wherein the lower alcohol is ethanol.

13. The method according to claim 9, wherein the fatty acid ester is isopropyl myristate or isopropyl palmitate.

14. The method according to claim 9, wherein the glycerin fatty acid ester is glyceryl monocaprylate, glyceryl monocaprate, or glyceryl monolaurate.

15. The method according to claim 14, wherein the glycerin fatty acid ester is glyceryl monocaprylate or glyceryl monocaprate.

16. The method according to claim 9, wherein the adhesive is one or more selected from the group consisting of acrylic resins, silicone resins, styrene isoprene block copolymers, aliphatic hydrocarbon resins, alicyclic saturated hydrocarbon resins, terpene resins, rosin ester resins, and polyisobutylene resins.

* * * * *